United States Patent
Korber et al.

(10) Patent No.: US 9,855,329 B2
(45) Date of Patent: Jan. 2, 2018

(54) MOSAIC HIV ENVELOPE IMMUNOGENIC POLYPEPTIDES

(71) Applicants: Los Alamos National Security, LLC, polypeptides or compositions to a subject infected with HIV or at risk of HIV infection. In some embodiments, the methods include inducing an immune response to HIV in a subject comprising administering to the subject at least one (such as two, three, or more) of the immunogenic polypeptides or at least one (such as two, three, or more) nucleic acids encoding at least one of the immunogenic polypeptides disclosed herein.

13 Claims, 15 Drawing Sheets

(51) Int. Cl.
| | |
|---|---|
| *C07K 14/16* | (2006.01) |
| *C07K 16/10* | (2006.01) |
| *A61K 45/06* | (2006.01) |
| *C07K 14/005* | (2006.01) |
| *C12N 7/00* | (2006.01) |
| *A61K 39/00* | (2006.01) |

(52) U.S. Cl.
CPC ........ *C07K 14/162* (2013.01); *C07K 16/1063* (2013.01); *C12N 7/00* (2013.01); *A61K 2039/57* (2013.01); *C07K 2317/34* (2013.01); *C07K 2317/76* (2013.01); *C12N 2740/16034* (2013.01); *C12N 2740/16122* (2013.01); *C12N 2740/16134* (2013.01); *C12N 2740/16171* (2013.01)

(56) References Cited

U.S. PATENT DOCUMENTS

| | | |
|---|---|---|
| 2011/0305749 A1 | 12/2011 | Duch et al. |
| 2012/0231028 A1 | 9/2012 | Korber et al. |

OTHER PUBLICATIONS

Barouch et al., "Mosaic HIV-1 Vaccines Expand the Breadth and Depth of Cellular Immune Responses in Rhesus Monkeys," *Nat. Med.*, vol. 16, pp. 319-323, 2010 (15 pages, author manuscript version).

Fischer et al., "Polyvalent vaccines for optimal coverage of potential T-cell epitopes in global HIV-1 variants," *Nature Medicine*, vol. 13, No. 1, pp. 100-106 (2007).

Hanke et al., "HIV-1: From escapism to conservatism," *Eur. J. Immunol.*, vol. 41, pp. 3390-3393, 2011.

Letourneau et al., "Design and Pre-Clinical Evaluation of a Universal HIV-1 Vaccine," *PLoS One*, vol. 2, e984, 2007 (11 pages).

Santra et al. "Mosaic Vaccines Elicit CD8+ T lymphocyte Responses in Monkeys that Confer Enhanced Immune Coverage of Diverse HIV Strains," *Nat. Med.*, vol. 16, pp. 324-328, 2010 (13 pages, author manuscript version).

UniProtKB/TrEMBL C4MJI7 9HIV1, Feb. 8, 2011 (1 page).

UniProtKB/TrEMBL, Accession No. M4TF15_9HIV1, Jul. 24, 2014 (1 page).

* cited by examiner

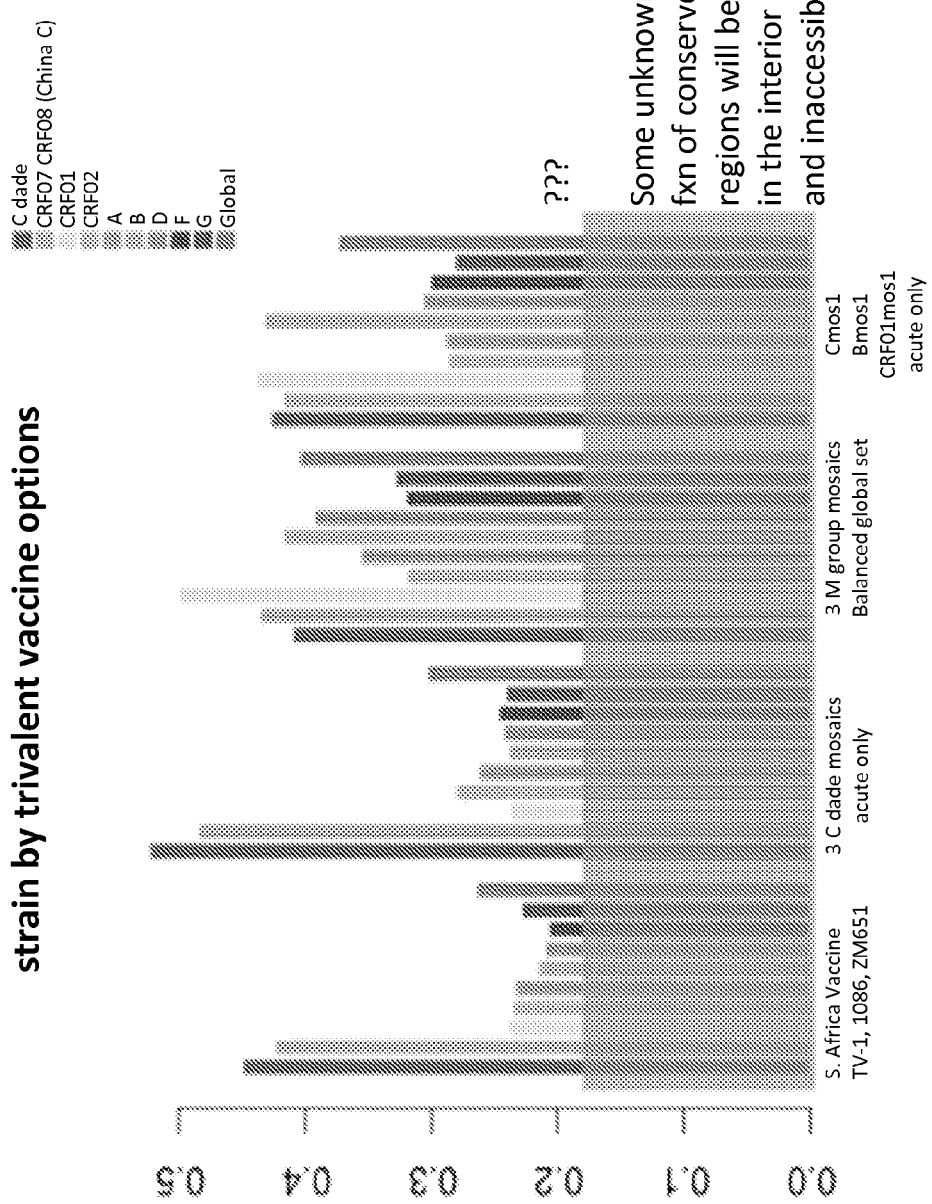

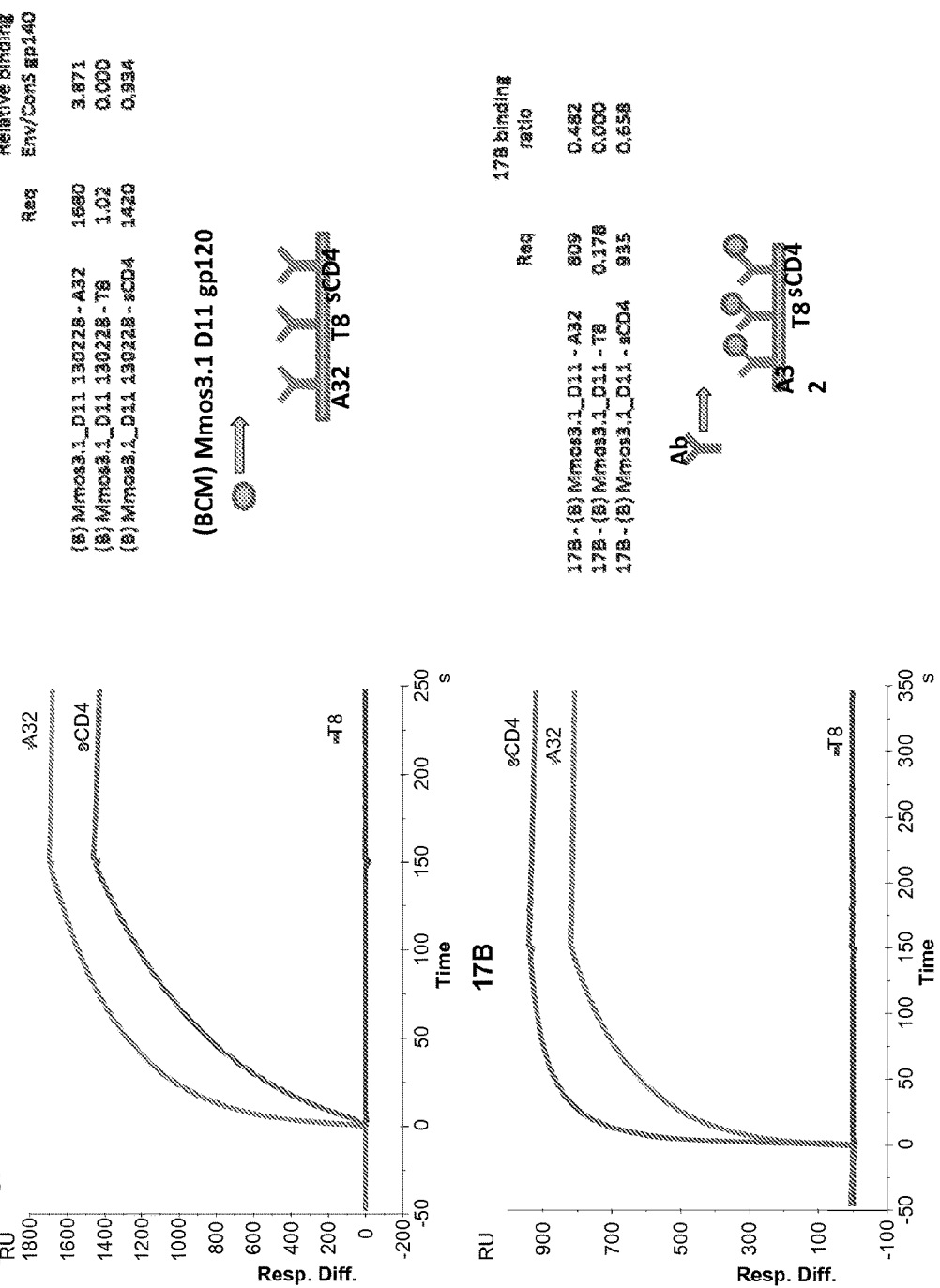

FIG. 11
Titration on 697D
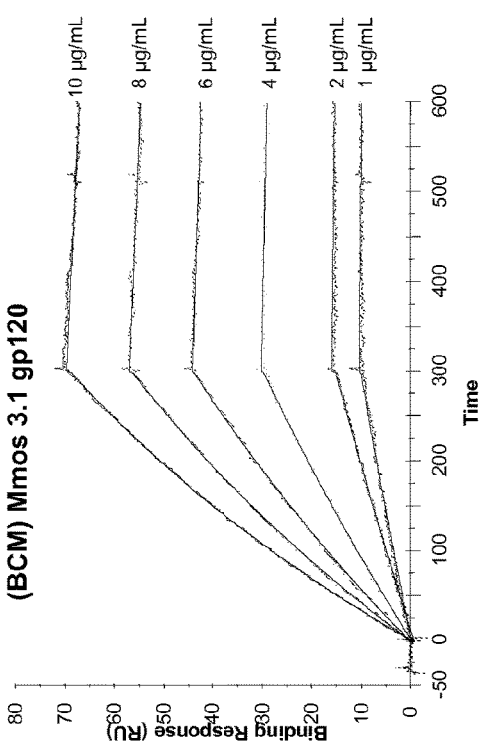
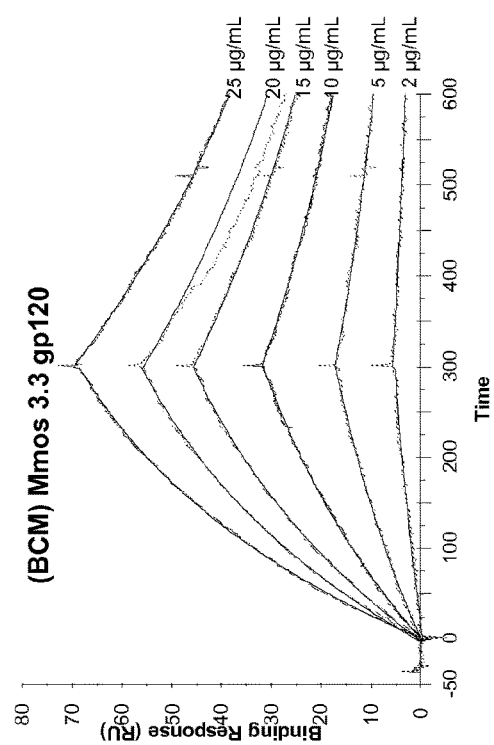
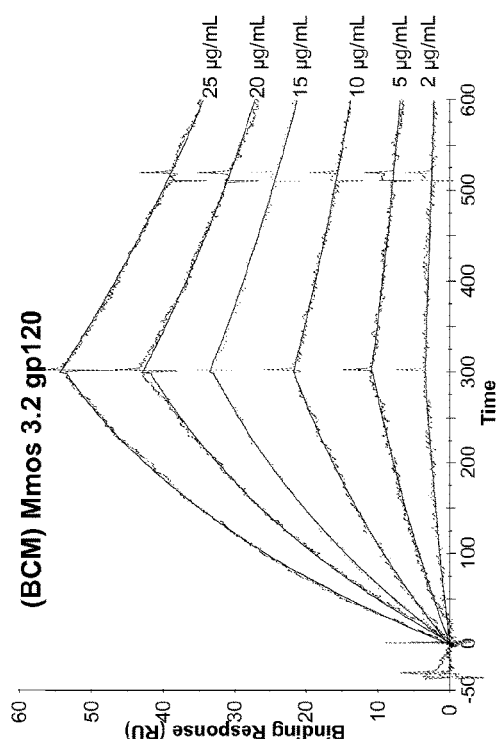

MOSAIC HIV ENVELOPE IMMUNOGENIC POLYPEPTIDES

CROSS REFERENCE TO RELATED APPLICATIONS

This is the §371 U.S. National Stage of International Application No. PCT/US2014/058443, filed Sep. 30, 2014, which was published in English under PCT Article 21(2), which in turn claims the benefit of U.S. Provisional Application No. 61/884,696, filed Sep. 30, 2013, which is incorporated by reference herein in its entirety.

ACKNOWLEDGMENT OF GOVERNMENT SUPPORT

This invention was made with government support under Contract No. DE-AC52-06NA25396 awarded by the U.S. Department of Energy and grant number AI100645 from the National Institutes of Health. The government has certain rights in the invention.

FIELD

This disclosure relates to immunogenic polypeptides, particularly polypeptides that can elicit an immune response to human immunodeficiency virus (HIV) in a subject.

BACKGROUND

Approximately 35 million people worldwide are estimated to be infected with human immunodeficiency virus (HIV). Although infection rates are declining, in 2012 about 2.3 million people were newly infected and about 1.6 million people died from AIDS-related illnesses. However, viral diversity in HIV and the occurrence of escape variants provide significant challenges to development of effective HIV vaccines. Thus, there remains a need for the development of effective vaccines to treat and inhibit HIV infection worldwide.

SUMMARY

Disclosed herein are mosaic HIV envelope (Env) proteins that can elicit an immune response to HIV (such as cytotoxic T cell (CTL), helper T cell, and/or humoral responses). In specific examples, the disclosed mosaic proteins (also referred to herein as mosaic Env proteins or immunogenic polypeptides) can elicit B cell responses to HIV. Also disclosed are sets of mosaic Env proteins, which include two or more (for example, three or more) of the proteins. In some embodiments, the disclosed mosaic Env proteins or sets of mosaic Env proteins are included in an immunogenic composition, such as a polyvalent immunogenic composition.

Also disclosed herein are methods for treating or inhibiting HIV in a subject including administering one or more of the disclosed immunogenic polypeptides or compositions to a subject infected with HIV or at risk of HIV infection. In some embodiments, the methods include inducing an immune response to HIV in a subject, comprising administering to the subject at least one (such as two, three, or more) of the disclosed immunogenic polypeptides or at least one (such as two, three, or more) nucleic acids encoding at least one of the immunogenic polypeptides disclosed herein.

The foregoing and other features of the disclosure will become more apparent from the following detailed description, which proceeds with reference to the accompanying figures.

BRIEF DESCRIPTION OF THE DRAWINGS

In FIGS. 2A and 2C, the Env trimer is viewed from the perspective of the target cell. In FIGS. 2B and 2D, the trimer is shown from a perspective parallel to the viral membrane. The density map is shown as a blue mesh.

FIG. 3 is a plot showing 10 amino acid cluster coverage per strain by each of the trivalent polypeptide options. For each trivalent polypeptide option, the strains are shown in the order (left to right): C clade, CRF07 CRF08 (China C), CRF01, CRF02, A, B, D, F, G, Global. The first two on the left of each group are C clade and China CRF07 and CFR08, that are basically C clade in Env, respectively. Within clade, three naturals do very well in terms of C clade potential epitope coverage; however the C clade mosaic performs slightly better. The inter-clade coverage is poor for either of these C clade-specific compositions. An advantage of the M group design (which is based on the global diversity or HIV-1, rather than a single clade) is that the C clade coverage is comparable to within-clade, but all other clades are simultaneously well covered, so the potential to be a global vaccine is enhanced.

FIG. 5 shows the relative binding of Mmos3.1 to 17b, a monoclonal antibody which is CD4-inducible and mimics the CCR5 co-receptor binding, after binding to CD4. The graph shows the ratio of 17b relative to ConS after binding to A32, sCD4, and T8. ConS is an HIV consensus protein that is particularly sensitive to CD4 induction of the 17b binding site. A32 is a monoclonal antibody that mimics CD4 in this process, and T8 is a control.

FIG. 11 shows a series of plots of SPR titration of Mmos3.1, Mmos3.2, and Mmos 3.3 with V2-region clade specific antibody 697D.

SEQUENCE LISTING

Figure 1:
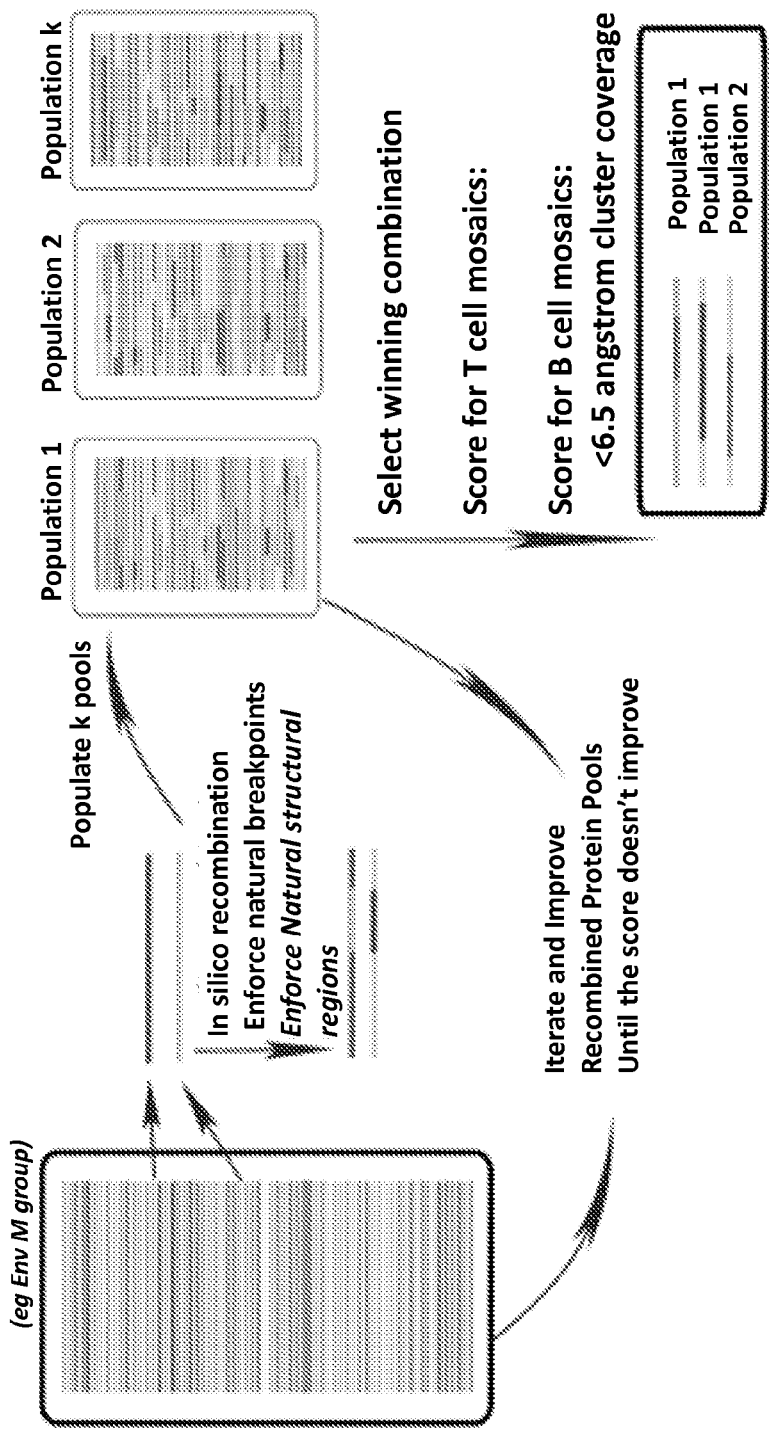
FIG. 1 is a schematic diagram showing an exemplary approach to mosaic B cell epitope design.
Figure 2A:
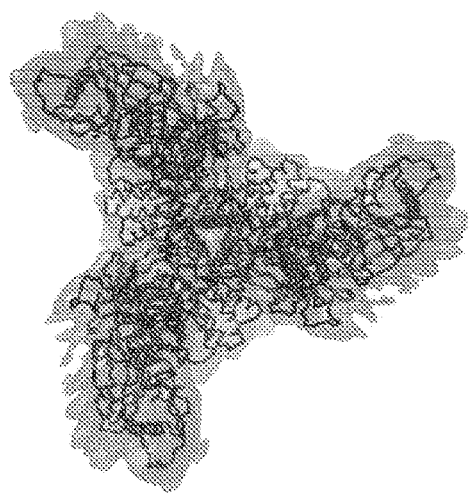
FIGS. 2A-2D are a series of diagrams showing the draft Ca trace of the unliganded HIV -$1_{JR-FL}$ Env trimer. The Ca trace is shown as a backbone worm. The backbone worms of all three protomers are shown in FIGS. 2A and 2B, and the backbone worm of one protomer is shown in FIGS. 2C and 2D.
Figure 2B:
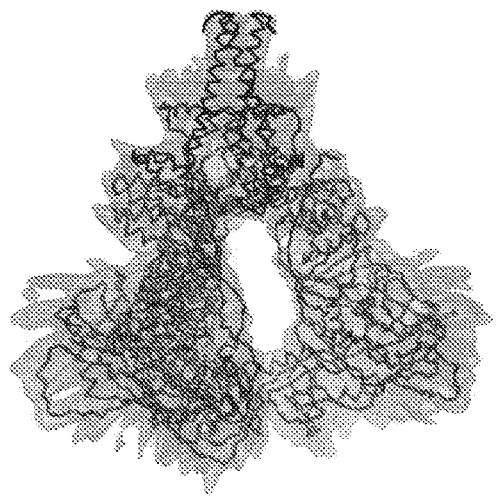
Figure 2C:
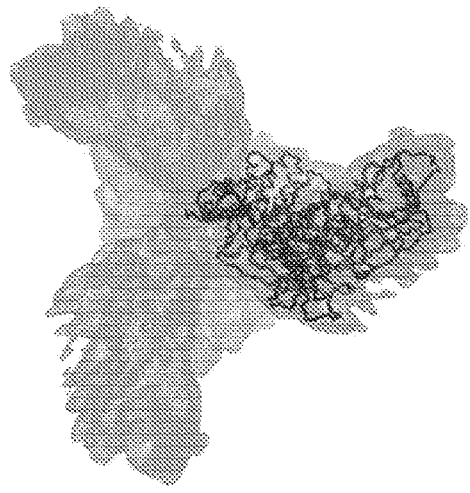
Figure 2D:
Figure 4A:
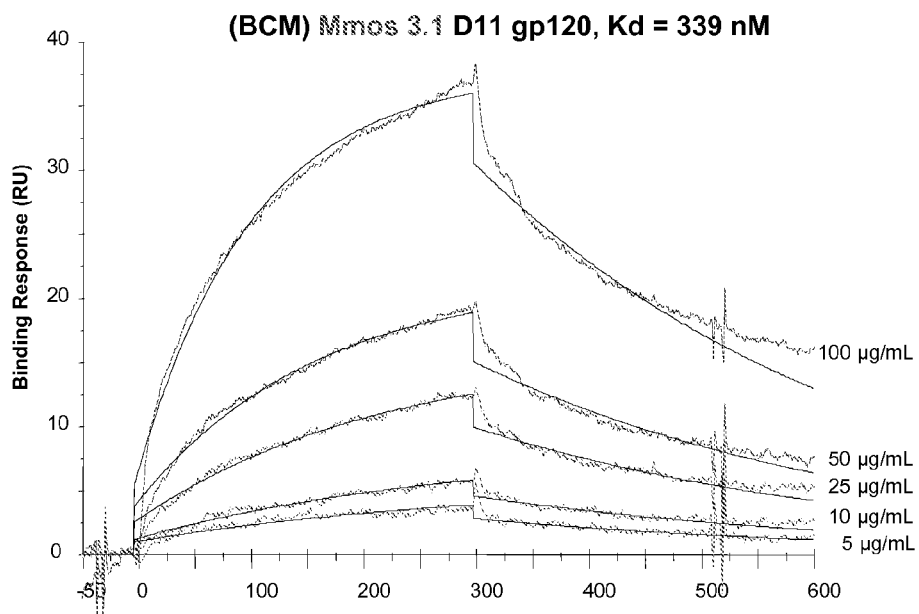
FIGS. 4A-4C are a series of plots showing titration of Mmos3.1 (FIG. 4A), Mmos3.2 (FIG. 4B), and Mmos 3.3 (FIG. 4C) with the HIV-neutralizing monoclonal antibody PG9, using surface plasmon resonance (SPR) (Hearty, Methods Mol. Biol. 907:411-42, 2012). The slow off rate of PG9 when bound to Mos3.2 is indicated by the gradual decline after the peak.
Figure 4B:
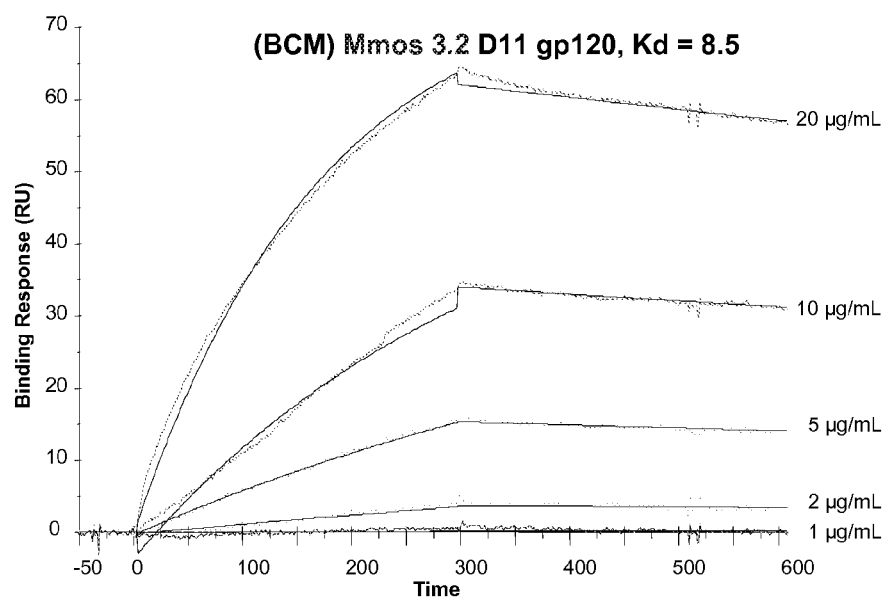
Figure 4C:
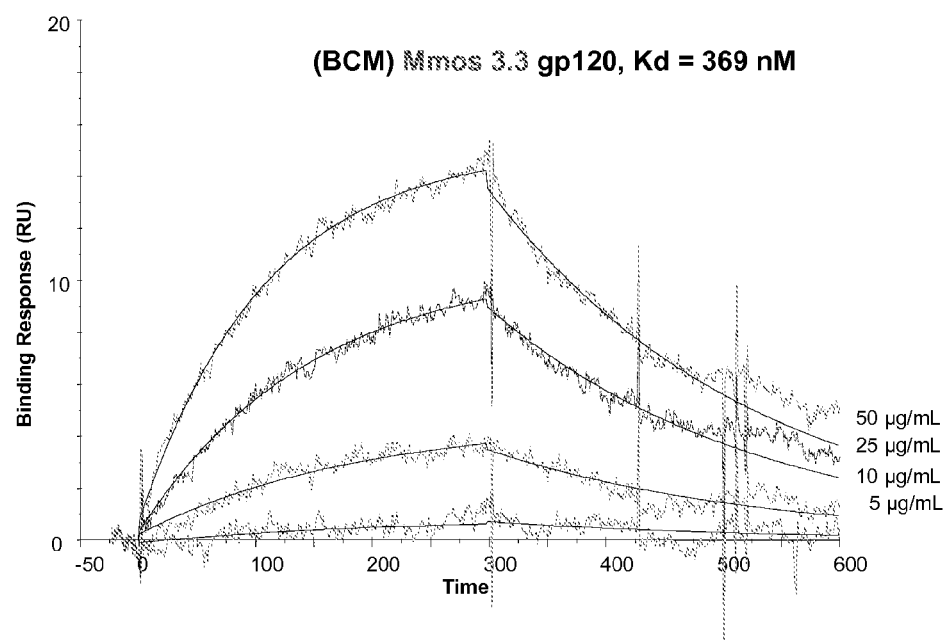
Figure 6:
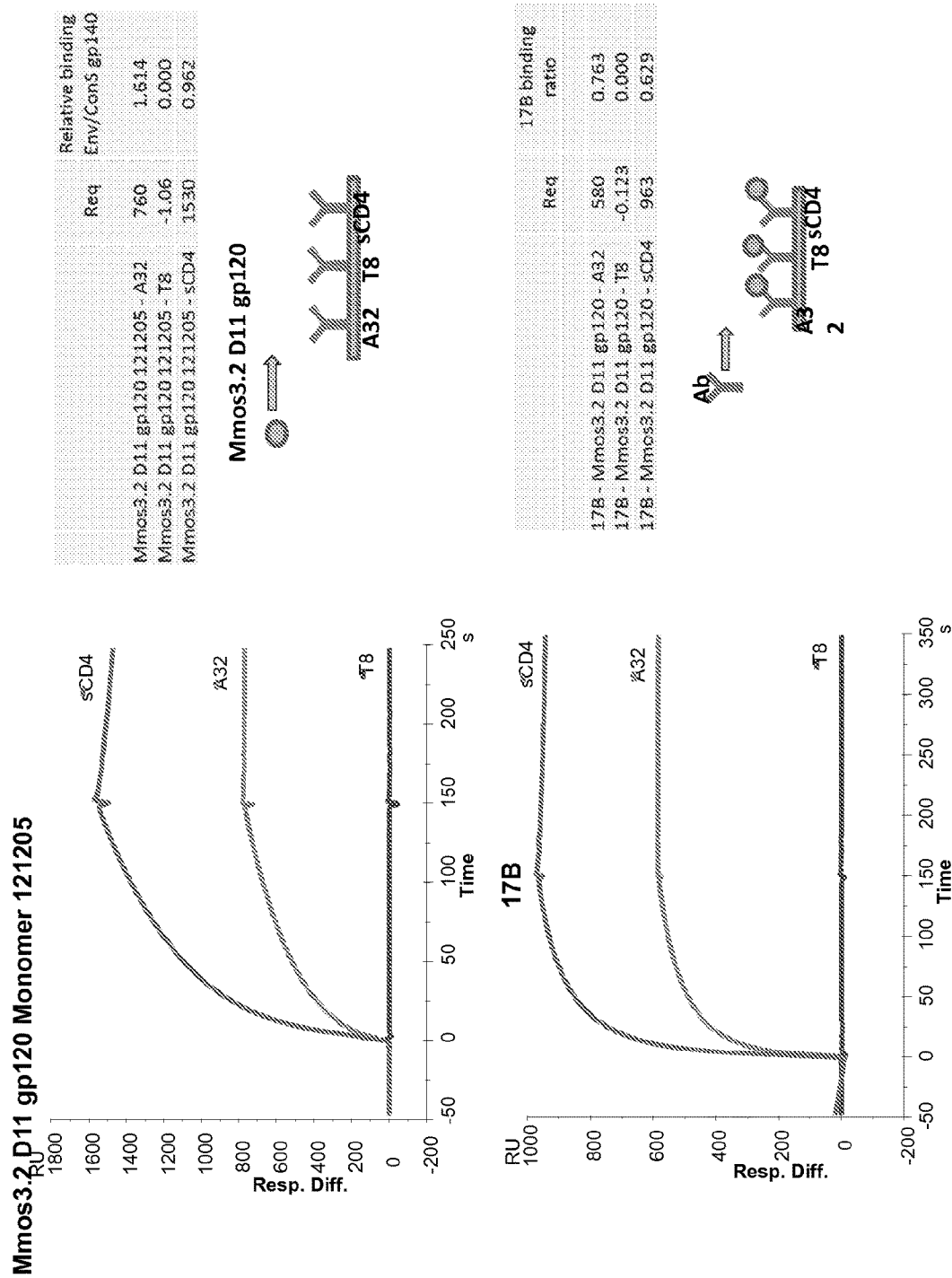
FIG. 6 shows the relative binding of Mmos3.2 to 17b compared with ConS after binding to A32, sCD4, and T8, as described in FIG. 5.
Figure 7:
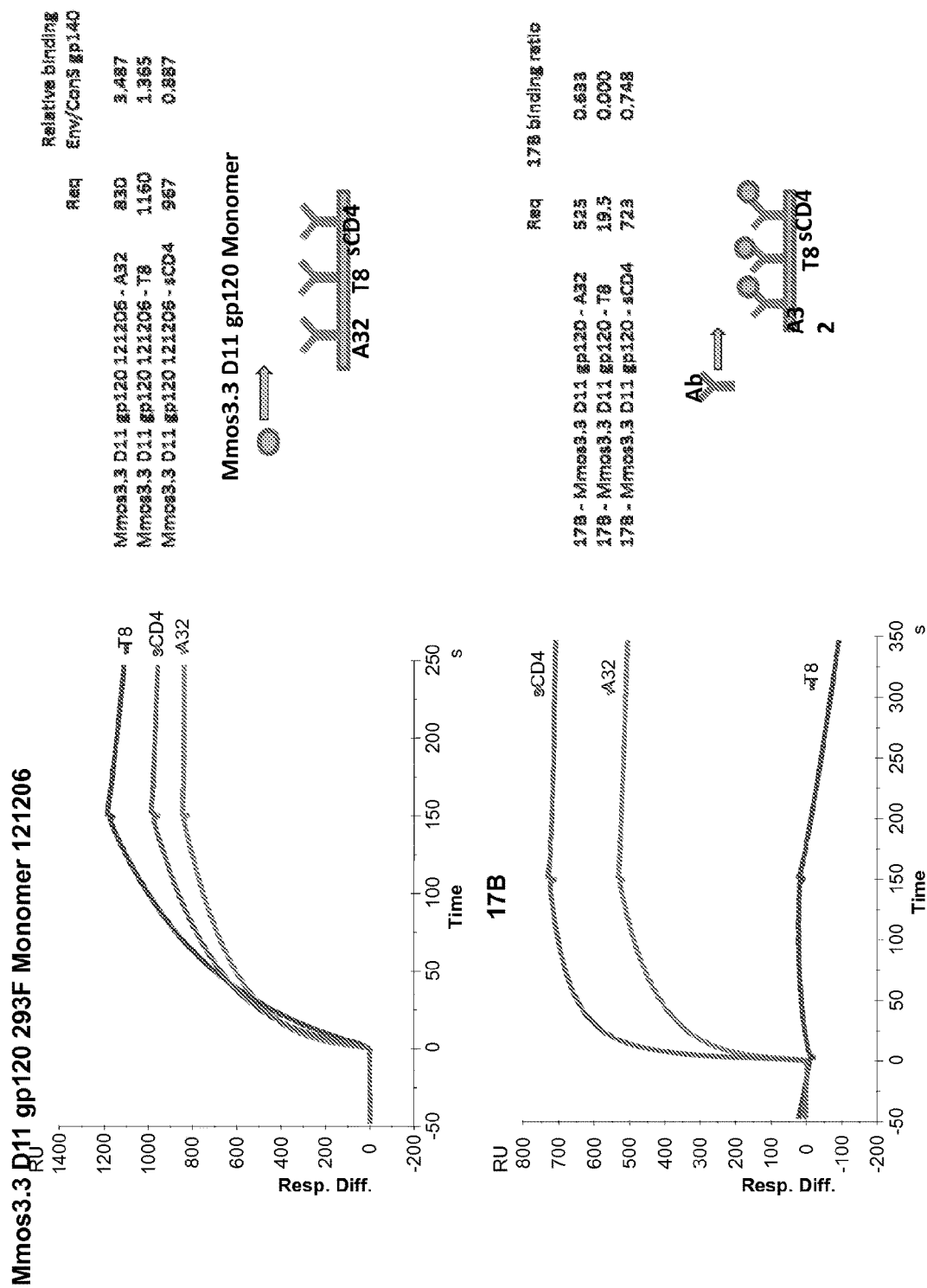
FIG. 7 shows the relative binding of Mmos3.3 to 17b compared with ConS after binding to A32, sCD4, and T8 as described in FIG. 5.
Figure 8:
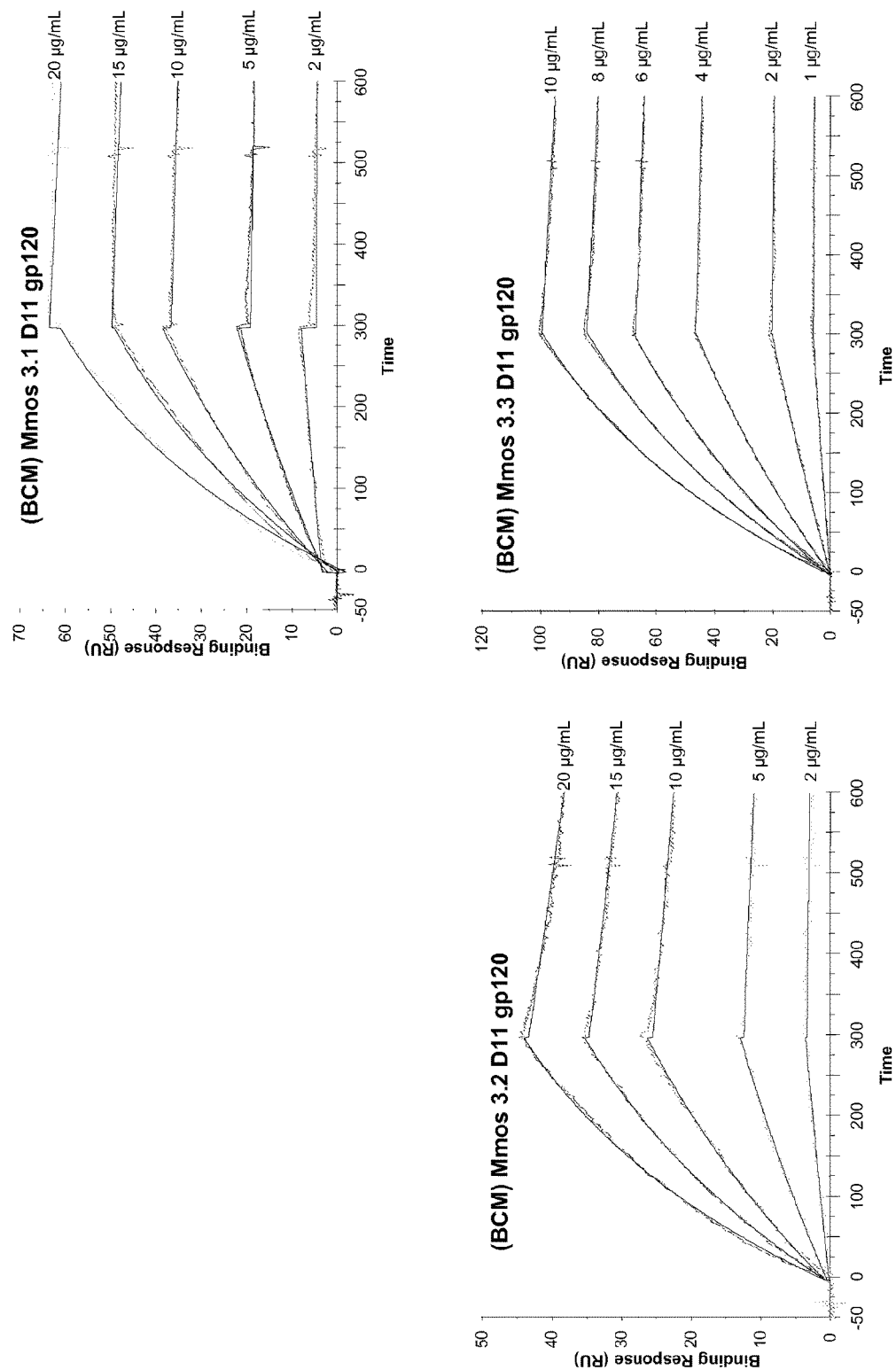
FIG. 8 shows a series of plots of SPR titration of Mmos3.1, Mmos3.2, and Mmos 3.3 binding to CD4 binding site targeting neutralizing antibody VRC01.
Figure 9:
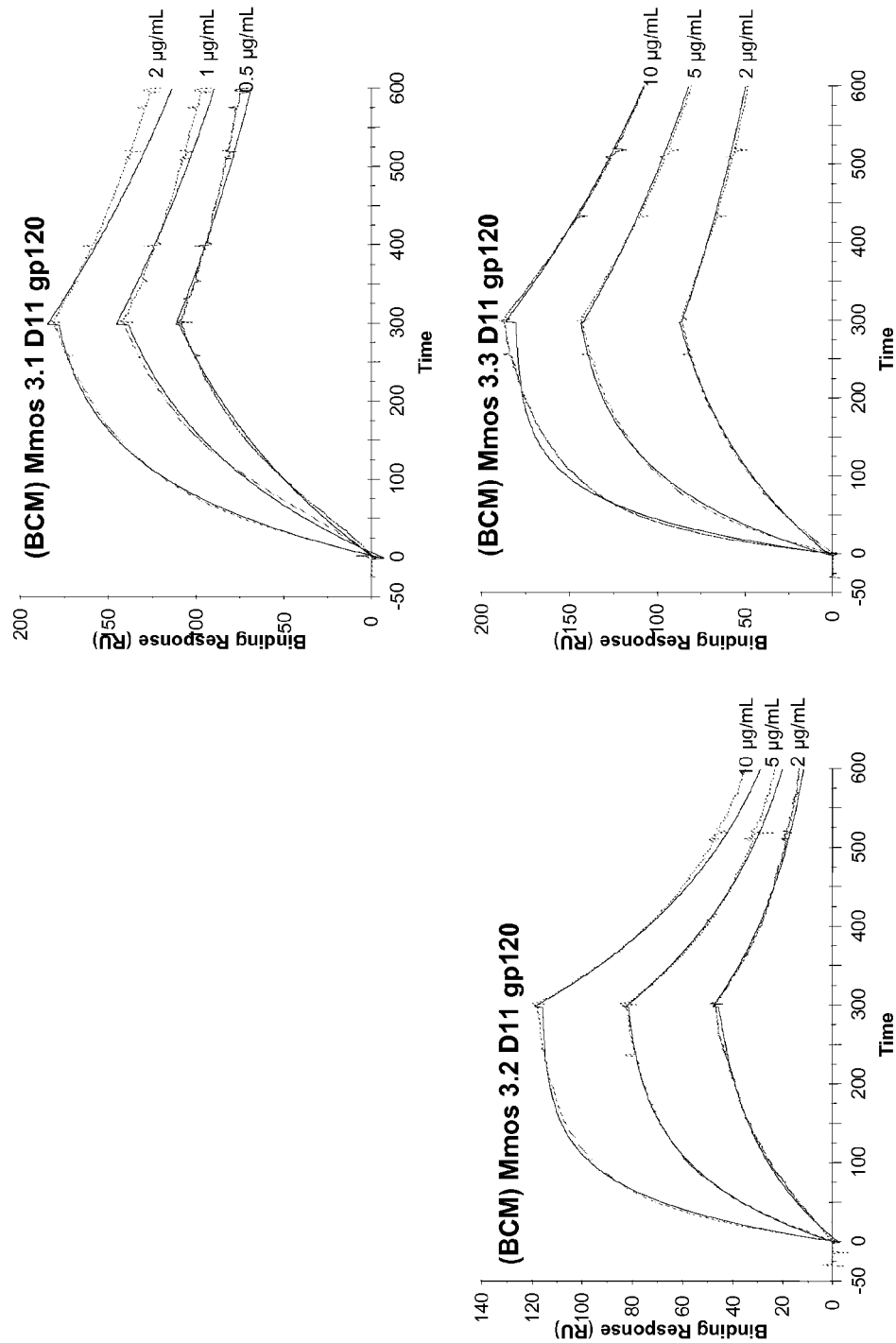
FIG. 9 shows a series of plots of SPR titration of Mmos3.1, Mmos3.2, and Mmos 3.3 with V3 region antibody 19b.
Figure 10:
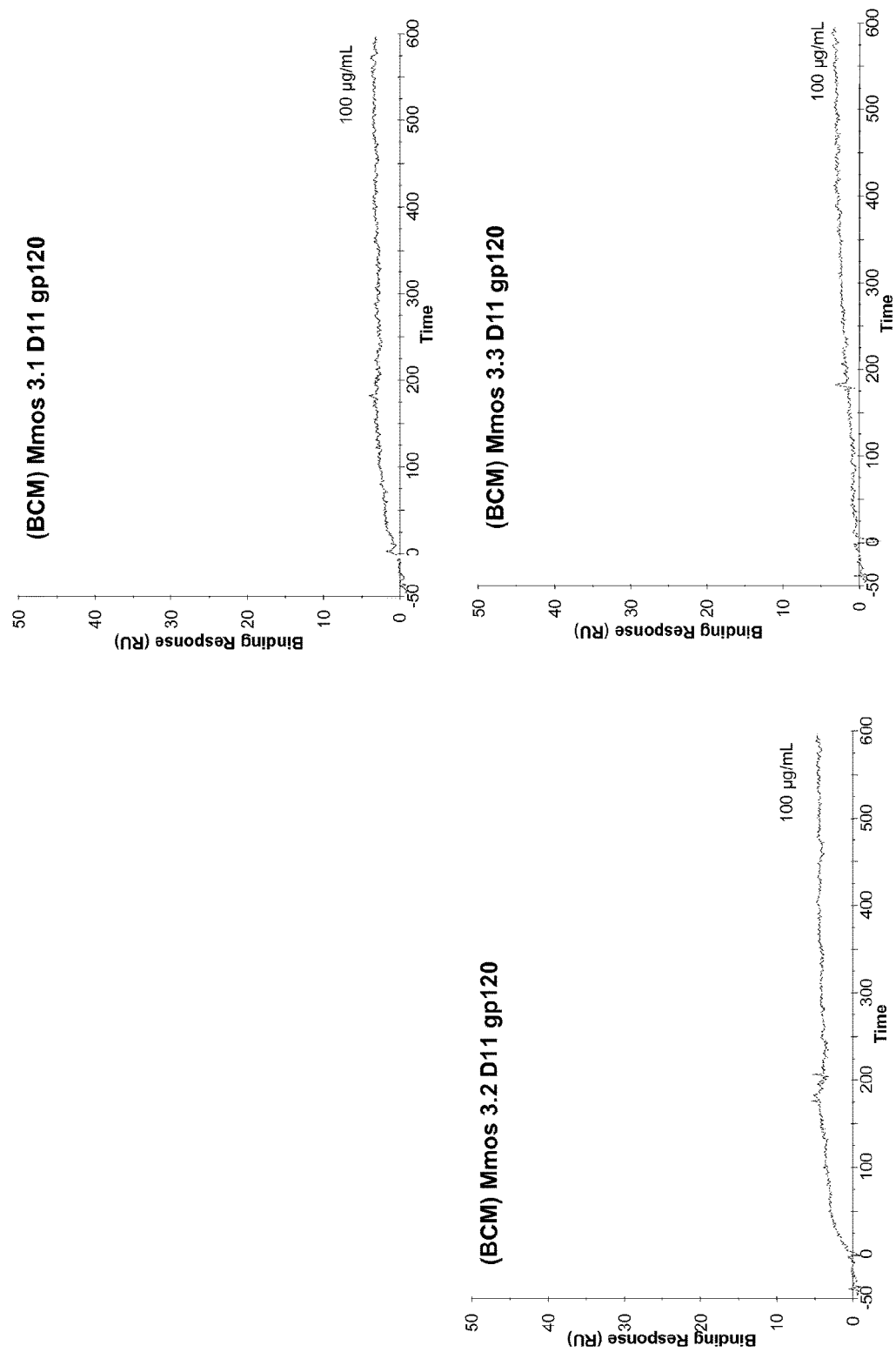
FIG. 10 shows a series of plots of SPR titration of Mmos3.1, Mmos3.2, and Mmos 3.3 with HIV V1-V2 glycan binding neutralizing antibody CH02. CH01 failed to bind to the mosaic proteins.
Figure 12:
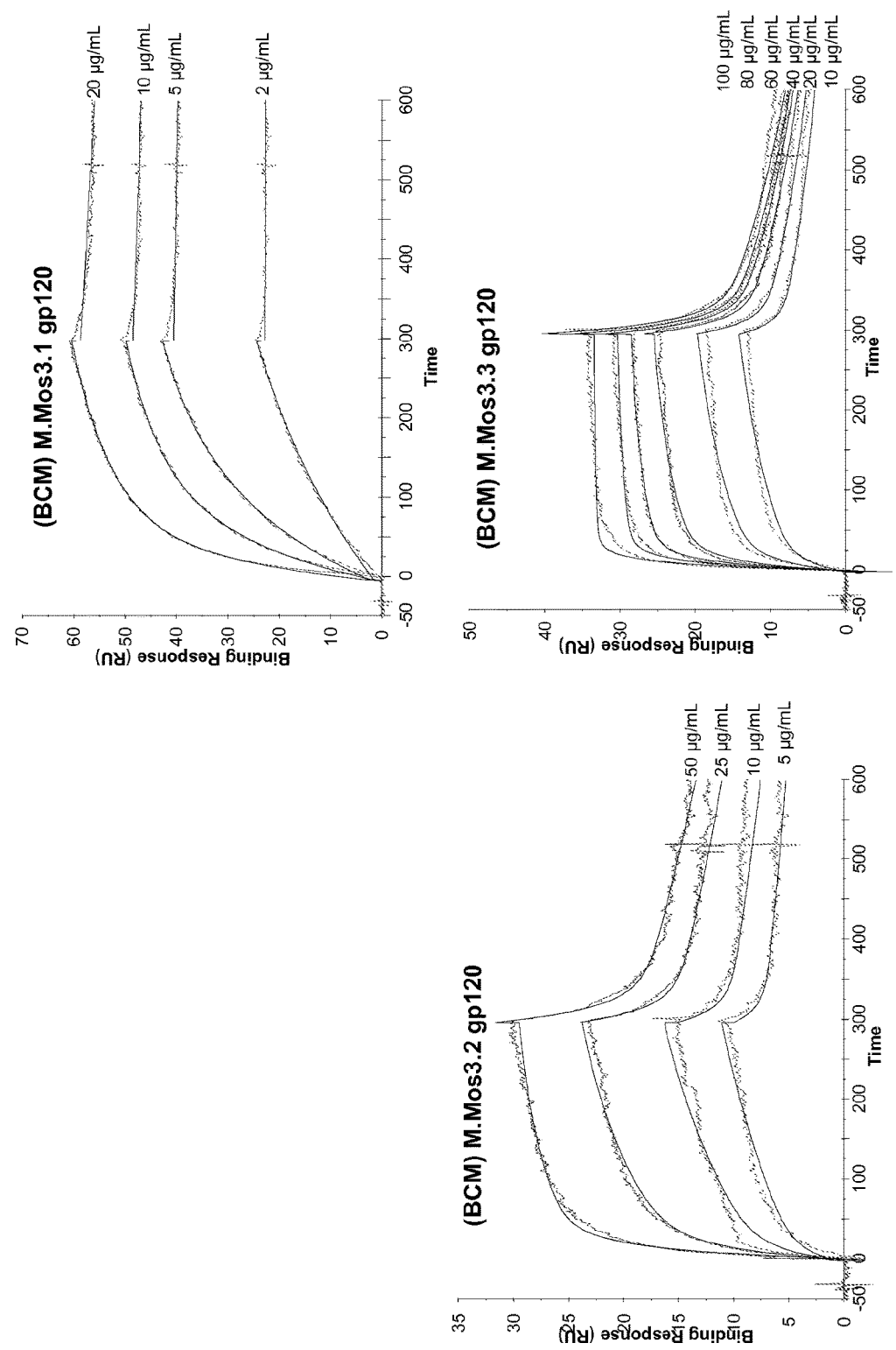
FIG. 12 shows a series of plots of SPR titration of Mmos3.1, Mmos3.2, and Mmos 3.3 with HIV carbohydrate binding neutralizing antibody 2G12.
Figure 13:
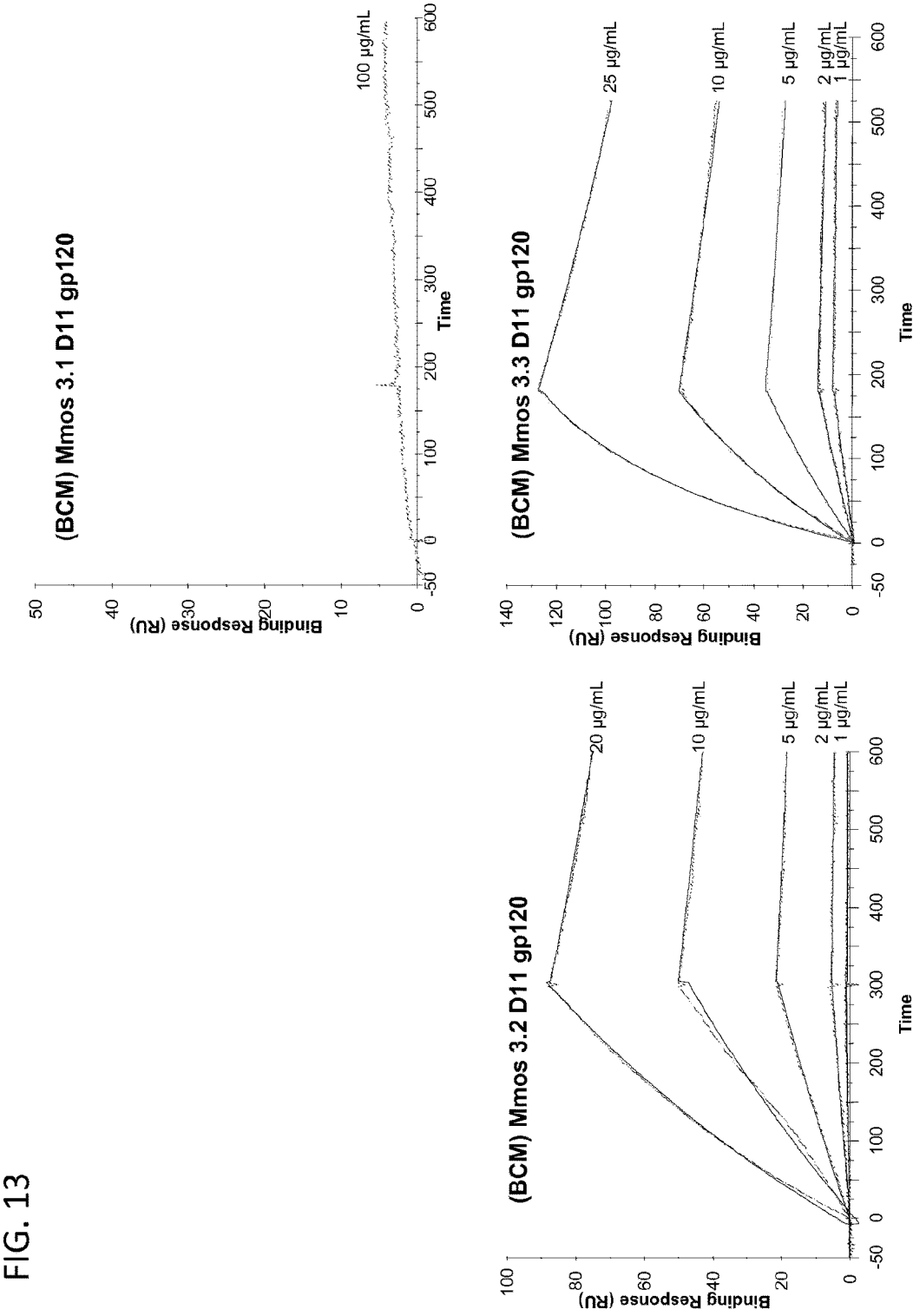
FIG. 13 shows a series of plots of SPR titration of Mmos3.1, Mmos3.2, and Mmos 3.3 with the HIV specific monoclonal antibody CH58.
Figure 14:
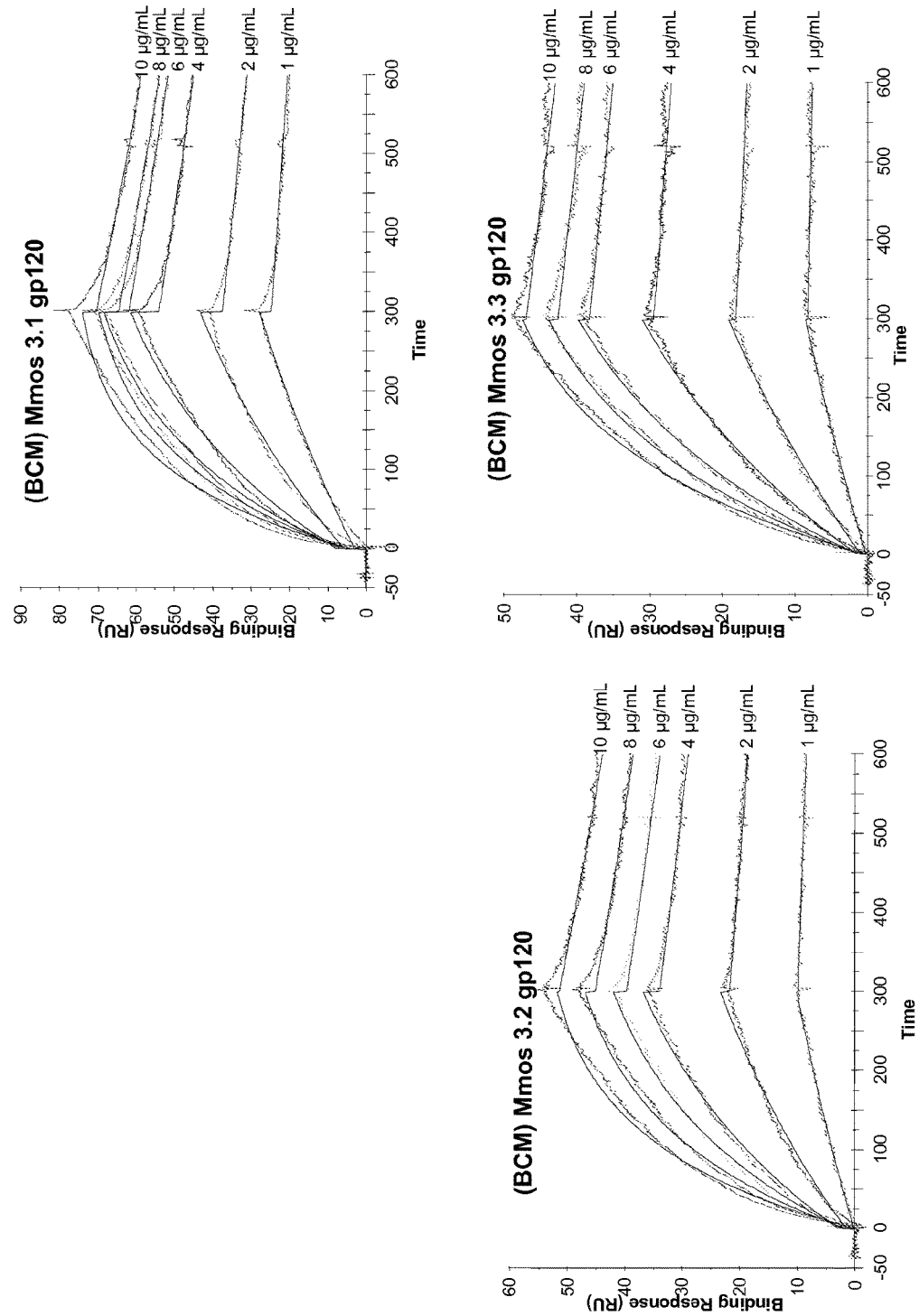
FIG. 14 shows a series of plots of SPR titration of Mmos3.1, Mmos3.2, and Mmos 3.3 with the potent HIV neutralizing antibody PGT128.

The nucleic acid and amino acid sequences disclosed herein and in the accompanying Sequence Listing are shown using standard letter abbreviations for nucleotide bases, and one letter code for amino acids. Only one strand of each nucleic acid sequence is shown, but the complementary strand is understood as included by any reference to the displayed strand.

The Sequence Listing is submitted as an ASCII text file in the form of the file named Sequence_Listing.txt, which was created on Mar. 22, 2016, and is 59,531 bytes, which is incorporated by reference herein.

SEQ ID NOs: 1-8 are the amino acid sequence of exemplary Env mosaic proteins.

SEQ ID NO: 9 is the amino acid sequence of a tissue plasminogen activator leader peptide.

DETAILED DESCRIPTION

I. Terms

Unless otherwise noted, technical terms are used according to conventional usage. Definitions of common terms in molecular biology can be found in Benjamin Lewin, *Genes VII*, published by Oxford University Press, 1999; Kendrew et al. (eds.), *The Encyclopedia of Molecular Biology*, published by Blackwell Science Ltd., 1994; and Robert A. Meyers (ed.), *Molecular Biology and Biotechnology: a Comprehensive Desk Reference*, published by VCH Publishers, Inc., 1995; and other similar references.

As used herein, the singular forms "a," "an," and "the," refer to both the singular as well as plural, unless the context clearly indicates otherwise. For example, the term "an antigen" includes single or plural antigens and can be considered equivalent to the phrase "at least one antigen." As used herein, the term "comprises" means "includes." Thus, "comprising an antigen" means "including an antigen" without excluding other elements.

It is further to be understood that any and all base sizes or amino acid sizes, and all molecular weight or molecular mass values, given for nucleic acids or polypeptides are approximate, and are provided for descriptive purposes, unless otherwise indicated. Although many methods and materials similar or equivalent to those described herein can be used, particular suitable methods and materials are described below. In case of conflict, the present specification, including explanations of terms, will control. In addition, the materials, methods, and examples are illustrative only and not intended to be limiting.

To facilitate review of the various embodiments of the disclosure, the following explanations of terms are provided:

Adjuvant: A vehicle used to enhance antigenicity. Adjuvants include a suspension of minerals (alum, aluminum hydroxide, or phosphate) on which antigen is adsorbed; or water-in-oil emulsion in which antigen solution is emulsified in mineral oil (Freund incomplete adjuvant), sometimes with the inclusion of killed mycobacteria (Freund's complete adjuvant) to further enhance antigenicity (inhibits degradation of antigen and/or causes influx of macrophages). Immunostimulatory oligonucleotides (such as those including a CpG motif) can also be used as adjuvants (for example see U.S. Pat. Nos. 6,194,388; 6,207,646; 6,214,806; 6,218,371; 6,239,116; 6,339,068; 6,406,705; and 6,429,199). Adjuvants include biological molecules (a "biological adjuvant"), such as costimulatory molecules. Exemplary biological adjuvants include IL-2, RANTES, GM-CSF, TNF-$\alpha$, IFN-$\gamma$, G-CSF, LFA-3, CD72, B7-1, B7-2, OX-40L and 41 BBL. Adjuvants can be used in combination with the disclosed immunogenic polypeptides.

Administration: The introduction of a composition into a subject by a chosen route. For example, if the chosen route is intravenous, the composition (such as a disclosed antigen) is administered by introducing the composition intravenously into a subject.

Antibody: A polypeptide substantially encoded by an immunoglobulin gene or immunoglobulin genes, or fragments thereof, which specifically binds and recognizes an analyte (such as an antigen or immunogen) such as a Env polypeptide or antigenic fragment thereof. Immunoglobulin genes include the kappa, lambda, alpha, gamma, delta, epsilon and mu constant region genes, as well as the myriad immunoglobulin variable region genes.

Antibodies exist, for example as intact immunoglobulins and as a number of well characterized fragments produced by digestion with various peptidases. For instance, Fabs, Fvs, and single-chain Fvs (SCFvs) that bind to Env would be Env-specific binding agents. This includes intact immunoglobulins and the variants and portions of them well known in the art, such as Fab' fragments, F(ab)'$_2$ fragments, single chain Fv proteins (scFv), and disulfide stabilized Fv proteins (dsFv). A scFv protein is a fusion protein in which a light chain variable region of an immunoglobulin and a heavy chain variable region of an immunoglobulin are bound by a linker, while in dsFvs, the chains have been mutated to introduce a disulfide bond to stabilize the association of the chains. The term antibody also includes genetically engineered forms such as chimeric antibodies (such as humanized murine antibodies), heteroconjugate antibodies (such as bispecific antibodies). See also, *Pierce Catalog and Handbook*, 1994-1995 (Pierce Chemical Co., Rockford, Ill.); Kuby, J., *Immunology*, 3$^{rd}$ Ed., W.H. Freeman & Co., New York, 1997.

Antibody fragments are defined as follows: (1) Fab, the fragment which contains a monovalent antigen-binding fragment of an antibody molecule produced by digestion of whole antibody with the enzyme papain to yield an intact light chain and a portion of one heavy chain; (2) Fab', the fragment of an antibody molecule obtained by treating whole antibody with pepsin, followed by reduction, to yield an intact light chain and a portion of the heavy chain; two Fab' fragments are obtained per antibody molecule; (3) (Fab')$_2$, the fragment of the antibody obtained by treating whole antibody with the enzyme pepsin without subsequent reduction; (4) F(ab')$_2$, a dimer of two Fab' fragments held together by two disulfide bonds; (5) Fv, a genetically engineered fragment containing the variable region of the light chain and the variable region of the heavy chain expressed as two chains; and (6) single chain antibody (SCA), a genetically engineered molecule containing the variable region of the light chain, the variable region of the heavy chain, linked by a suitable polypeptide linker as a genetically fused single chain molecule. The term "antibody" as used herein, also includes antibody fragments either produced by the modification of whole antibodies or those synthesized de novo using recombinant DNA methodologies.

Typically, a naturally occurring immunoglobulin has heavy (H) chains and light (L) chains interconnected by disulfide bonds. There are two types of light chain, lambda (λ) and kappa (κ). There are five main heavy chain classes (or isotypes) which determine the functional activity of an antibody molecule: IgM, IgD, IgG, IgA and IgE. Each heavy and light chain contains a constant region and a variable region, (the regions are also known as "domains"). In combination, the heavy and the light chain variable regions specifically bind the antigen. Light and heavy chain variable regions contain a "framework" region interrupted by three hypervariable regions, also called "complementarity-determining regions" or "CDRs." The extent of the framework region and CDRs have been defined (see, Kabat et al., *Sequences of Proteins of Immunological Interest*, U.S. Department of Health and Human Services, 1991, which is hereby incorporated by reference). The Kabat database is now maintained online. The sequences of the framework regions of different light or heavy chains are relatively conserved within a species. The framework region of an antibody, that is the combined framework regions of the constituent light and heavy chains, serves to position and align the CDRs in three-dimensional space.

The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, a $V_H$ CDR3 is located in the variable domain of the heavy chain of the antibody in which it is found, whereas a $V_L$ CDR1 is the CDR1 from the variable domain of the light chain of the antibody in which it is found. Light chain CDRs are sometimes referred to as CDR L1, CDR L2, and CDR L3. Heavy chain CDRs are sometimes referred to as CDR H1, CDR H2, and CDR H3.

References to "$V_H$" or "VH" refer to the variable region of an immunoglobulin heavy chain, including that of an Fv, scFv, dsFv or Fab. References to "$V_L$" or "VL" refer to the variable region of an immunoglobulin light chain, including that of an Fv, scFv, dsFv or Fab.

A "monoclonal antibody" is an antibody produced by a single clone of B-lymphocytes or by a cell into which the light and heavy chain genes of a single antibody have been transfected. Monoclonal antibodies are produced by methods known to those of skill in the art, for instance by making hybrid antibody-forming cells from a fusion of myeloma cells with immune spleen cells. These fused cells and their progeny are termed "hybridomas." Monoclonal antibodies include humanized monoclonal antibodies.

Antigen: A compound, composition, or substance that can stimulate the production of antibodies or a T cell response in a subject, including compositions that are injected or absorbed into a subject. An antigen reacts with the products of specific humoral or cellular immunity, including those induced by heterologous antigens, such as the disclosed antigens. "Epitope" or "antigenic determinant" refers to the region of an antigen to which B and/or T cells respond. In one embodiment, T cells respond to the epitope, when the epitope is presented in conjunction with an MHC molecule. Epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5, about 9, about 8-10, or about 6-22 amino acids in a unique spatial conformation. Methods of determining spatial conformation of epitopes include, for example, x-ray crystallography and nuclear magnetic resonance.

Examples of antigens include, but are not limited to, peptides, lipids, polysaccharides, and nucleic acids containing antigenic determinants, such as those recognized by an immune cell. In some examples, antigens include peptides derived from a pathogen of interest. Exemplary pathogens include bacteria, fungi, viruses and parasites. In specific examples, an antigen is derived from HIV, for example, one or more HIV polypeptides or a fragment thereof, such as at least a portion of an Env protein.

B cell: A lymphocyte, a type of white blood cell that expresses immunoglobulin on its surface and can ultimately develop into an antibody secreting a plasma cell. In one example, a B cell expresses CD19 (CD19+). An "immature B cell" is a cell that can develop into a mature B cell. Generally, pro-B cells (that express, for example, CD45 or B220) undergo immunoglobulin heavy chain rearrangement to become pre-B pre-B cells, and further undergo immunoglobulin light chain rearrangement to become an immature B cells. Immature B cells include T1 and T2 B cells. Immature B cells express IgM on their cell surface and can develop into mature B cells, which can express different forms of immunoglobulin (e.g., IgA, IgG). B cells can be activated by agents such as lipopolysaccharide (LPS), CD40 ligation, and antibodies that crosslink the B cell receptor (immunoglobulin), including antigen, or anti-Ig antibodies. Neutralizing antibodies can inhibit HIV infection of the natural viral target cell, CD4 positive T cells.

Envelope (Env): The envelope protein from HIV. Env is initially synthesized as a precursor protein of 845-870 amino acids in size (gp160). gp160 forms a homotrimer and undergoes glycosylation in the Golgi apparatus. It is then cleaved by a cellular protease into gp120 and gp41. gp120 includes most of the surface-exposed domains of the Env glycoprotein complex and binds to the cellular CD4 receptor and cellular chemokine receptors (for example, CCR5). Env is the only HIV protein capable of stimulating HIV neutralizing antibodies.

HXB2 numbering system: A reference numbering system for HIV protein and nucleic acid sequences, which uses HIV-1 HXB2 strain sequences as a reference for all other HIV strain sequences. The person of ordinary skill in the art is familiar with the HXB2 numbering system (Korber et al., Human Retroviruses and AIDS 1998: A Compilation and Analysis of Nucleic Acid and Amino Acid Sequences. Korber B, Kuiken C L, Foley B, Hahn B, McCutchan F, Mellors J W, and Sodroski J, Eds.; Theoretical Biology and Biophysics Group, Los Alamos National Laboratory, Los Alamos, N.M., incorporated by reference herein in its entirety). HXB2 is also known as: HXBc2, for HXB clone 2; HXB2R, in the Los Alamos HIV database, with the R for revised, as it was slightly revised relative to the original HXB2 sequence; and HXB2CG in the NCBI GenBank database, for HXB2 complete genome.

Host cells: Cells in which a virus or vector can be propagated and its DNA expressed. The cell may be prokaryotic or eukaryotic. The term also includes any progeny of the subject host cell. It is understood that all progeny may not be identical to the parental cell since there may be mutations that occur during replication. However, such progeny are included when the term "host cell" is used.

Immunogenic polypeptide: A protein or a portion thereof that is capable of inducing an immune response in a subject, such as a subject infected with, or at risk of infection with, a pathogen. Administration of an immunogenic polypeptide derived from a pathogen of interest can elicit an immune response against the pathogen. Administration of an immunogenic polypeptide can lead to protective immunity against a pathogen of interest (such as HIV). In some examples, an immunogenic polypeptide is a polypeptide including one or more regions from an HIV proteome, for example, an Env protein, such as a mosaic Env protein.

Immune response: A response of a cell of the immune system, such as a B cell, T cell, or monocyte, to a stimulus. In one embodiment, the response is specific for a particular antigen (an "antigen-specific response"). In one embodiment, an immune response is a T cell response, such as a CD4+ response or a CD8+ response. In another embodiment, the response is a B cell response, and results in the production of specific antibodies. Some HIV neutralizing antibody responses can be type-specific, and only elicit responses that neutralize a single strain, while others are broad and can elicit responses to many different strains.

Immunogenic composition: A composition comprising an immunogenic polypeptide or a nucleic acid encoding an immunogenic polypeptide that induces a measurable CTL response against virus expressing the immunogenic polypeptide or a portion thereof, induces a measurable helper T cell response, or induces a measurable B cell response (such as production of antibodies) against the immunogenic polypeptide or a portion thereof. In one example, an "immunogenic composition" is composition including one or more polypeptides from HIV, such as one or more of the mosaic Env proteins disclosed herein. It further refers to isolated nucleic acids encoding an immunogenic polypeptide, such as a nucleic acid that can be used to express the immunogenic polypeptide (and thus be used to elicit an immune response against this polypeptide or a portion thereof).

For in vitro use, an immunogenic composition may consist of at least one (such as two or more) isolated polypeptides, peptide epitopes, or nucleic acids encoding the polypeptide or peptide epitope. For in vivo use, the immunogenic composition will typically include at least one (such as one, two, three, or more) polypeptide, peptide, or nucleic acid in pharmaceutically acceptable carriers, and/or other agents. Any particular peptide, such as a disclosed polypeptide or a nucleic acid encoding the polypeptide, can be readily tested for its ability to induce a CTL, helper T cell, or B cell response by art-recognized assays. Immunogenic compositions can include adjuvants, which are well known to one of skill in the art.

Inhibiting or treating a disease: Inhibiting the full development of a disease or condition, for example, in a subject who is at risk for a disease such as acquired immune deficiency syndrome (AIDS), AIDS-related conditions, HW infection (such as HIV-1 infection), or combinations thereof. "Treatment" refers to a therapeutic intervention that ameliorates a sign or symptom of a disease or pathological condition (such as AIDS or AIDS related conditions) after it has begun to develop. The term "ameliorating," with reference to a disease or pathological condition, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, an improvement in the overall health or well-being of the subject, or by other parameters well known in the art that are specific to the particular disease. A "prophylactic" treatment is a treatment administered to a subject who does not exhibit signs of a disease or exhibits only early signs for the purpose of decreasing the risk of developing pathology.

Isolated: An "isolated" biological component (such as a protein, for example a disclosed polypeptide or nucleic acid encoding such a polypeptide) has been substantially separated or purified away from other biological components in which the component naturally occurs, such as other chromosomal and extrachromosomal DNA, RNA, and proteins. Proteins, peptides, and nucleic acids that have been "isolated" include proteins purified by standard purification methods. The term also embraces proteins or peptides prepared by recombinant expression in a host cell as well as chemically synthesized proteins, peptides, and nucleic acid molecules.

Isolated does not require absolute purity, and can include protein, peptide, or nucleic acid molecules that are at least 50% isolated, such as at least 75%, 80%, 90%, 95%, 98%, 99%, or even 99.9% isolated.

Mosaic polypeptide or mosaic protein: A polypeptide or protein assembled from fragments of natural sequences via computational optimization (e.g., Fischer et al., *Nat. Med.* 13:100-106, 2007). Multiple sequences (for example, thousands of sequences) are used as input and the sequences are evolved by recombination in silico. Recombinants are constrained to have natural breakpoints and a mosaic set is designed to maximize coverage of potential epitopes (such as B cell epitopes) for a viral population.

Operably linked: A first nucleic acid is operably linked with a second nucleic acid when the first nucleic acid is placed in a functional relationship with the second nucleic acid. For instance, a promoter is operably linked to a coding sequence if the promoter affects the transcription or expression of the coding sequence. Generally, operably linked nucleic acids are contiguous and, where necessary to join two protein-coding regions, in the same reading frame. In some examples, the operably linked nucleic acids are heterologous, for example, the first and second nucleic acids are from different organisms, different genes, or different polypeptides and the resulting nucleic acid is not naturally occurring.

Pharmaceutically acceptable carriers: The pharmaceutically acceptable carriers useful in this disclosure are conventional. *Remington: The Science and Practice of Pharmacy*, The University of the Sciences in Philadelphia, Editor, Lippincott, Williams, & Wilkins, Philadelphia, Pa., 21$^{st}$ Edition (2005), describes compositions and formulations suitable for pharmaceutical delivery of the proteins, nucleic acids, and other compositions herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions, powder, pill, tablet, or capsule forms, conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Polypeptide: Any compound composed of amino acids and/or amino acid analogs, chemically bound together. Polypeptide as used herein includes oligomers of amino acids and/or amino acid analogs, or small and large peptides, including proteins. Any chain of amino acids, regardless of length or post-translational modification (such as glycosylation or phosphorylation) is referred to as a polypeptide. The term polypeptide applies to amino acid polymers including naturally occurring amino acid polymers and non-naturally occurring amino acid polymers as well as polymers in which one or more amino acid residue is a non-natural amino acid, for example an artificial chemical mimetic of a corresponding naturally occurring amino acid. As used herein, polypeptide also refers to recombinant amino acid polymers, such as polymers including portions that are obtained from different (typically non-contiguous) portions of a genome (such as an HIV genome) and/or are obtained from different genomes (such as two or more HIV strains). A "residue" refers to an amino acid or amino acid mimetic incorporated in a polypeptide by an amide bond or amide bond mimetic.

Polyvalent immunogenic composition: A composition including two or more separate immunogenic polypeptides (such as a "cocktail" of immunogenic polypeptides) that are capable of eliciting an immune response in a subject, for example an immune response to HIV. In some examples, a polyvalent immunogenic composition includes two or more immunogenic polypeptides (or nucleic acids encoding the polypeptides). In one specific example, a polyvalent immunogenic composition includes three Env proteins, such as three Env mosaic proteins disclosed herein.

Purified: The term purified does not require absolute purity; rather, it is intended as a relative term. Thus, for example, a purified protein is one in which the protein is more enriched than the protein is in its natural environment within a cell. Preferably, a preparation is purified such that the protein represents at least 50% of the protein content of the preparation.

Recombinant nucleic acid or polypeptide: A nucleic acid molecule or polypeptide that is not naturally occurring or has a sequence that is made by an artificial combination of two otherwise separated segments of nucleotide or amino acid sequence. This artificial combination is accomplished by chemical synthesis or by the artificial manipulation of isolated segments of nucleic acids, e.g., by genetic engineering techniques such as those described in Sambrook et al. (ed.), *Molecular Cloning: A Laboratory Manual*, 2$^{nd}$ ed., vol. 1-3, Cold Spring Harbor Laboratory Press, Cold Spring Harbor, N.Y., 1989. The term "recombinant" includes nucleic acids or polypeptides that have been altered solely by addition, substitution, or deletion of a portion of a natural nucleic acid molecule or peptide.

Sequence identity/similarity: Sequence identity between two or more nucleic acid sequences or between two or more amino acid sequences can be measured in terms of percentage identity; the higher the percentage, the more identical the sequences are. Homologs or orthologs of nucleic acid or amino acid sequences possess a relatively high degree of sequence identity/similarity when aligned using standard methods.

Methods of alignment of sequences for comparison are well known in the art. Various programs and alignment algorithms are described in: Smith & Waterman, *Adv. Appl. Math.* 2:482, 1981; Needleman & Wunsch, *J. Mol. Biol.* 48:443, 1970; Pearson & Lipman, *Proc. Natl. Acad. Sci. USA* 85:2444, 1988; Higgins & Sharp, *Gene,* 73:237-44, 1988; Higgins & Sharp, *CABIOS* 5:151-3, 1989; Corpet et al., *Nuc. Acids Res.* 16:10881-90, 1988; Huang et al. *Computer Appls. in the Biosciences* 8, 155-65, 1992; and Pearson et al., *Meth. Mol. Bio.* 24:307-31, 1994. Altschul et al., *J. Mol. Biol.* 215:403-10, 1990, presents a detailed consideration of sequence alignment methods and homology calculations. The NCBI Basic Local Alignment Search Tool (BLAST) (Altschul et al., *J. Mol. Biol.* 215:403-10, 1990) is available from several sources, including the National Center for Biological Information (NCBI, National Library of Medicine, Building 38A, Room 8N805, Bethesda, Md. 20894) and on the Internet, for use in connection with the sequence analysis programs blastp, blastn, blastx, tblastn, and tblastx. Blastn is used to compare nucleic acid sequences, while blastp is used to compare amino acid sequences. Additional information can be found at the NCBI web site.

In some examples, sequence similarity is assessed by the conservation of epitope-length fragments. The use of this measure of similarity was developed at Los Alamos National Laboratory, and tools are available on the World Wide Web at hiv.lanl.gov.

Subject: Living multi-cellular vertebrate organisms, a category that includes both human and non-human mammals (including non-human primates).

Therapeutically effective amount or effective amount: The amount of an agent, such as a nucleic acid, polypeptide, or other therapeutic agent, that is sufficient to prevent, treat (including prophylaxis), reduce and/or ameliorate the symptoms and/or underlying causes of a disorder or disease, for example to prevent, inhibit, and/or treat HIV. In some embodiments, an "effective amount" is sufficient to reduce or eliminate a symptom of a disease, such as AIDS. For instance, this can be the amount necessary to inhibit viral replication or to measurably alter outward symptoms of the viral infection, such as an increase of T cell counts in the case of an HIV infection. In general, this amount will be sufficient to measurably inhibit virus (for example, HIV) replication or infectivity. An "anti-viral agent" or "anti-viral drug" is an agent that specifically inhibits a virus from replicating or infecting cells. Similarly, an "anti-retroviral agent" is an agent that specifically inhibits a retrovirus from replicating or infecting cells.

Transformed: A transformed cell is a cell into which has been introduced a nucleic acid molecule by molecular biology techniques. As used herein, the term transformation encompasses all techniques by which a nucleic acid molecule might be introduced into such a cell, including transfection with viral vectors, transformation with plasmid vectors, and introduction of DNA by electroporation, lipofection, and particle gun acceleration.

Vaccine: A pharmaceutical composition that elicits a prophylactic or therapeutic immune response in a subject. In some cases, the immune response is a protective immune response and can block subsequent infection, in other cases it can limit the pathological impact of an infection by containing the infection. Typically, a vaccine elicits an antigen-specific immune response to an antigen of a pathogen, for example a viral pathogen, or to a cellular constituent correlated with a pathological condition. A vaccine may include a polynucleotide (such as a nucleic acid encoding a disclosed antigen), a peptide or polypeptide (such as a disclosed antigen), a virus, a cell, or one or more cellular constituents.

Vector: A nucleic acid molecule that can be introduced into a host cell, thereby producing a transformed host cell. Recombinant DNA vectors are vectors having recombinant DNA. A vector can include nucleic acid sequences that permit it to replicate in a host cell, such as an origin of replication. A vector can also include one or more selectable marker genes and other genetic elements known in the art.

Viral vectors are recombinant DNA vectors having at least some nucleic acid sequences derived from one or more viruses.

Virus: A virus consists essentially of a core of nucleic acid surrounded by a protein coat, and has the ability to replicate only inside a living cell. "Viral replication" is the production of additional virus by the occurrence of at least one viral life cycle. A virus may subvert the host cell's normal functions, causing the cell to behave in a manner determined by the virus. For example, a viral infection may result in a cell producing a cytokine, or responding to a cytokine, when the uninfected cell does not normally do so. In some examples, a virus is a pathogen.

"Retroviruses" are RNA viruses wherein the viral genome is RNA. When a host cell is infected with a retrovirus, the genomic RNA is reverse transcribed into a DNA intermediate which is integrated very efficiently into the chromosomal DNA of infected cells. The integrated DNA intermediate is referred to as a provirus. The term "lentivirus" is used in its conventional sense to describe a genus of viruses containing reverse transcriptase. The lentiviruses include the "immunodeficiency viruses" which include human immunodeficiency virus (HIV) type 1 and type 2 (HIV-1 and HIV-2), simian immunodeficiency virus (SIV), and feline immunodeficiency virus (FIV).

HIV-1 is a retrovirus that causes immunosuppression in humans (HIV disease), and leads to a disease complex known as the acquired immunodeficiency syndrome (AIDS). "HIV disease" refers to a well-recognized constellation of signs and symptoms (including the development of opportunistic infections) in persons who are infected by an HIV virus, as determined by antibody or western blot studies or detection of HIV nucleic acids. Laboratory findings associated with this disease are a progressive decline in T cells.

II. Description of Several Embodiments

Disclosed herein are mosaic polypeptides from HIV Env protein (also referred to herein as immunogenic polypeptides). The mosaic polypeptides (also referred to as mosaic proteins) are computationally designed to optimally cover global HIV diversity (e.g., having the potential to elicit broadly cross-reactive immune responses), as described in Examples 1 and 2, below. Mosaic polypeptides are assembled from fragments of natural sequences via a computational optimization method (e.g., U.S. Pat. App. Publ. No. 2012/0231028, incorporated herein by reference in its entirety). In some embodiments, mosaic polypeptides resemble natural proteins, but do not exist in nature. Thousands of sequences are use used as input, and the sequences are evolved by recombination in silico. Recombinants are constrained to have natural breakpoints, and a mosaic set will maximize the coverage of potential epitopes (such as B cell epitopes) for a viral population. Combinations of mosaics are selected to give the optimal coverage of potential epitopes found in natural sequences for a given number of mosaics. The Env mosaic proteins and nucleic acids encoding the proteins disclosed herein are capable of eliciting an immune response to HIV in a subject.

Also disclosed herein are sets of the immunogenic polypeptides (such as sets of two or more polypeptides) that can be used to elicit an immune response to HIV in a subject. B cells undergo a process called affinity maturation, where they evolve to improve affinity for their target epitope during the immune response. Without being bound by theory, it is believed that by administering a set of Env polypeptides including coverage of multiple HIV variants to a subject, exposing a B cell lineage to common variants of an HIV epitope during affinity maturation may yield an antibody response with greater breadth and ability to interact with natural variants, by selecting for antibodies that high affinity for the most common forms of the epitope.

A. Immunogenic Polypeptides

Exemplary amino acid sequences of HIV Env mosaic proteins identified as described in Example 2 include SEQ ID NOs: 1-8 disclosed herein. In some examples, the disclosed polypeptides include, consist essentially of, or consist of an amino acid sequence at least 95% identical to the amino acid sequence set forth as one of SEQ ID NOs: 1-8, such as at least 95% identical, at least 96% identical, at least 97% identical, at least 98% identical, at least 99% identical, or even 100% identical to the sequence set forth as one of SEQ ID NOs: 1-8.

In some embodiments, the disclosed Env mosaic proteins are utilized in combination, for example as sets of immunogenic polypeptides. In some examples, the set of Env mosaic proteins includes 2, 3, 4, 5, 6, 7, or 8 of the disclosed polypeptides. The sets of polypeptides are selected for providing coverage of variants within a single HIV clade (for example, within clade C), providing coverage of variants between clades (for example, at least clade B, clade C, and CRF01), and/or global coverage (for example M group), and can be administered to a subject, for example as a polyvalent immunogenic composition. Exemplary sets of polypeptides are shown in Table 1. However, additional combinations of the disclosed immunogenic polypeptides can also be selected to produce additional sets.

TABLE 1

Exemplary sets of Env mosaic polypeptides

| Set | Polypeptides |
| --- | --- |
| Within Clade C | SEQ ID NO: 1, SEQ ID NO: 2, SEQ ID NO: 3 |
| Three clade | SEQ ID NO: 1, SEQ ID NO: 4, SEQ ID NO: 5 |
| Global | SEQ ID NO: 6, SEQ ID NO: 7, SEQ ID NO: 8 |

In some examples, a leader or signal peptide is linked to the immunogenic polypeptide, for example to increase expression and/or immunogenicity of the polypeptide. In one example, the leader peptide is a tissue plasminogen activator (tPA) leader peptide, for example, a peptide having the amino acid sequence MDAMKRGLCCVLLLC-GAVFVSAR (SEQ ID NO: 9). One of skill in the art can identify other suitable leader peptides that can be used to optimize expression of the disclosed polypeptides.

The immunogenic polypeptides disclosed herein can be chemically synthesized by standard methods, or can be produced recombinantly, for example by expression of the polypeptide from a nucleic acid molecule that encodes the polypeptide. An exemplary process for polypeptide production is described in Lu et al., *FEBS Lett.* 429:31-35, 1998. They can also be isolated by methods including preparative chromatography and immunological separations.

B. Nucleic Acids

Nucleic acids encoding the disclosed Env mosaic proteins (e.g., SEQ ID NOs: 1-8) are also disclosed herein. Unless otherwise specified, a "nucleic acid encoding a polypeptide" includes all nucleotide sequences that are degenerate versions of each other and encode the same amino acid sequence. For example, a polynucleotide encoding a disclosed immunogenic polypeptide includes a nucleic acid sequence that is degenerate as a result of the genetic code.

There are 20 natural amino acids, most of which are specified by more than one codon. Therefore, all degenerate nucleotide sequences are included as long as the amino acid sequence of the polypeptide encoded by the nucleotide sequence is unchanged. In some embodiments, the disclosed polypeptide sequences are back-translated to codon optimized DNA using standard methods.

The nucleic acids encoding a disclosed polypeptide include a recombinant DNA which is incorporated into a vector, such as an autonomously replicating plasmid or virus, or into the genomic DNA of a prokaryote or eukaryote, or which exists as a separate molecule (such as a cDNA) independent of other sequences. Methods for the manipulation and insertion of the nucleic acids of this disclosure into vectors are well known in the art (see for example, Sambrook et al., *Molecular Cloning, a Laboratory Manual*, 2d edition, Cold Spring Harbor Press, Cold Spring Harbor, N.Y., 1989, and Ausubel et al., *Current Protocols in Molecular Biology*, Greene Publishing Associates and John Wiley & Sons, New York, N.Y., 1994). DNA sequences encoding the polypeptide can be expressed in vitro or in vivo by DNA transfer into a suitable host cell. The cell may be prokaryotic or eukaryotic. Methods of stable transfer, meaning that the foreign DNA is continuously maintained in the host, are known in the art.

Polynucleotide sequences encoding the disclosed polypeptides can be operatively linked to expression control sequences. An expression control sequence operatively linked to a coding sequence is joined such that expression of the coding sequence is achieved under conditions compatible with the expression control sequences. The expression control sequences include, but are not limited to, appropriate promoters, enhancers, transcription terminators, a start codon (i.e., ATG) in front of a protein-encoding gene, splicing signal for introns, maintenance of the correct reading frame of that gene to permit proper translation of mRNA, and stop codons.

Hosts can include microbial, yeast, insect and mammalian organisms. Methods of expressing DNA sequences having eukaryotic or viral sequences in prokaryotes are well known in the art. Non-limiting examples of suitable host cells include bacteria, archaea, insect, fungi (for example, yeast), plant, and animal cells (for example, mammalian cells, such as human). Exemplary cells of use include *Escherichia coli, Bacillus subtilis, Saccharomyces cerevisiae, Salmonella typhimurium*, SF9 cells, C129 cells, *Neurospora*, and immortalized mammalian myeloid and lymphoid cell lines. Techniques for the propagation of mammalian cells in culture are well-known (see, Jakoby and Pastan (eds), 1979, Cell Culture, Methods in Enzymology, volume 58, Academic Press, Inc., Harcourt Brace Jovanovich, N.Y.). Examples of commonly used mammalian host cell lines are VERO and HeLa cells, CHO cells, HEK 293 cells, and WI38, BHK, and COS cell lines, although other cell lines may be used, such as cells designed to provide higher expression, desirable glycosylation patterns, or other features.

A number of viral vectors have been constructed, that can be used to express the disclosed polypeptides, including polyoma, i.e., SV40 (Madzak et al., 1992, *J. Gen. Virol.*, 73:1533-1536); adenovirus (Berkner, 1992, *Cur. Top. Microbiol. Immunol.*, 158:39-6; Berliner et al., 1988, *Bio Techniques*, 6:616-629; Gorziglia et al., 1992, *J. Virol.*, 66:4407-4412; Quantin et al., 1992, *Proc. Natl. Acad. Sci. USA*, 89:2581-2584; Rosenfeld et al., 1992, *Cell*, 68:143-155; Wilkinson et al., 1992, *Nucl. Acids Res.*, 20:2233-2239; Stratford-Perricaudet et al., 1990, *Hum. Gene Ther.*, 1:241-256); non-replicating adenoviruses of chimpanzee origin (ChAdv; Tatsis et al., *Gene Ther.* 13:421-429, 2006); vaccinia virus (Mackett et al., 1992, *Biotechnology*, 24:495-499); modified vaccinia Ankara (MVA) virus (Kremer et al., *Methods Mol. Biol.* 890:59-92, 2012); adeno-associated virus (Muzyczka, 1992, *Curr. Top. Microbiol. Immunol.*, 158:91-123; On et al., 1990, *Gene*, 89:279-282); herpes viruses, including HSV and EBV (Margolskee, 1992, *Curr. Top. Microbiol. Immunol.*, 158:67-90; Johnson et al., 1992, *J. Virol.*, 66:2952-2965; Fink et al., 1992, *Hum. Gene Ther.* 3:11-19; Breakfield et al., 1987, *Mol. Neurobiol.*, 1:337-371; Fresse et al., 1990, *Biochem. Pharmacol.*, 40:2189-2199); Sindbis viruses (Herweijer et al., 1995, *Human Gene Therapy* 6:1161-1167; U.S. Pat. Nos. 5,091,309 and 5,2217,879); alphaviruses (Schlesinger, 1993, *Trends Biotechnol.* 11:18-22; Frolov et al., 1996, *Proc. Natl. Acad. Sci. USA* 93:11371-11377); and retroviruses of avian (Brandyopadhyay et al., 1984, *Mol. Cell Biol.*, 4:749-754; Petropouplos et al., 1992, *J. Virol.*, 66:3391-3397), murine (Miller, 1992, *Curr. Top. Microbiol. Immunol.*, 158:1-24; Miller et al., 1985, *Mol. Cell Biol.*, 5:431-437; Sorge et al., 1984, *Mol. Cell Biol.*, 4:1730-1737; Mann et al., 1985, *J. Virol.*, 54:401-407), and human origin (Page et al., 1990, *J. Virol.*, 64:5370-5276; Buchschalcher et al., 1992, *J. Virol.*, 66:2731-2739). Baculovirus (*Autographa californica* multinuclear polyhedrosis virus; AcMNPV) vectors are also known in the art, and may be obtained from commercial sources (such as PharMingen, San Diego, Calif.; Protein Sciences Corp., Meriden, Conn.; Stratagene, La Jolla, Calif.).

III. Therapeutic Methods and Pharmaceutical Compositions

The immunogenic polypeptides disclosed herein (such as SEQ ID NOs: 1-8, or polypeptides having at least 95% sequence identity to SEQ ID NOs: 1-8), or nucleic acids encoding the disclosed immunogenic polypeptides, can be administered to a subject to elicit an immune response in the subject, such as an immune response to HIV. In some embodiments, one or more of the disclosed polypeptides (or one or more nucleic acids encoding the disclosed polypeptides) is administered to a subject with HIV infection or at risk of HIV infection. In other embodiments, the one or more immunogenic polypeptides are administered to a subject as part of an immunization regimen. The one or more immunogenic polypeptides are administered in an amount sufficient to elicit an immune response to HIV in the subject. In some examples, administration of the immunogenic peptide inhibits (or in some instances even prevents) infection with HIV and/or reduces the signs and symptoms of HIV in an infected subject.

In particular embodiments, two or more of the disclosed polypeptides or nucleic acids encoding the polypeptides are administered to the subject. In some examples, the methods include administering to the subject one or more Env mosaic proteins (or nucleic acids encoding at least two polypeptides), for example, as a polyvalent immunogenic composition. In particular examples, the methods include administering to the subject one or more of the Env mosaic proteins (for example, 2, 3, 4, 5, 6, 7, or more Env mosaic proteins) disclosed herein.

In some embodiments, a subject is administered a set of immunogenic polypeptides, such as a set of three immunogenic polypeptides disclosed herein. In one example, a set of immunogenic polypeptides administered to the subject includes three polypeptides comprising, consisting essentially of, or consisting of the amino acid sequences set forth as SEQ ID NO: 1, SEQ ID NO: 2, and SEQ ID NO: 3. In another example, a set of immunogenic polypeptides administered to the subject includes three polypeptides comprising, consisting essentially of, or consisting of the amino acid sequences set forth as SEQ ID NO: 1, SEQ ID NO: 4, and SEQ ID NO: 5. In a further example, a set of immunogenic polypeptides administered to the subject includes three polypeptides comprising, consisting essentially of, or consisting of the amino acid sequences set forth as SEQ ID NO: 6, SEQ ID NO: 7, and SEQ ID NO: 8. In additional examples, the C clade mosaic proteins disclosed herein could be used singly as SEQ ID NO: 1; as a pair of SEQ ID NO: 1 and SEQ ID NO: 2; or as a combination of all three proteins (SEQ ID NO: 1, SEQ ID NO: 2, and SEQ ID NO: 3) in a polyvalent vaccine. In further examples, SEQ ID NO: 4 or SEQ ID NO. 5 could be utilized singly or as a pair (for example in geographic regions where the B clade or CRF01 dominate the regional epidemic), as well as the three protein combination of SEQ ID NO: 1, SEQ ID NO: 4, and SEQ ID NO: 5. One of skill in the art can identify additional combinations of the disclosed polypeptides that could be administered to a subject as a set. In addition, the disclosed mosaic Env proteins can be combined with natural strains to form additional sets.

In some examples, the two or more immunogenic polypeptides (such as a set of immunogenic polypeptides) are administered simultaneously (for example, as a mixture), substantially simultaneously (for example, within a few minutes of one another, such as within less than 5 minutes of one another), or sequentially (for example, within 5 minutes, 10 minutes, 15 minutes, 30 minutes, 1 hour, 2 hours, 4 hours, 12 hours, 24 hours, or more of one another).

One or more of the disclosed polypeptides or nucleic acids encoding the polypeptides (including vectors including the nucleic acid) can be administered by any means known to one of skill in the art (see Banga, "Parenteral Controlled Delivery of Therapeutic Peptides and Proteins," in *Therapeutic Peptides and Proteins*, Technomic Publishing Co., Inc., Lancaster, Pa., 1995) either locally or systemically, such as by intramuscular, subcutaneous, or intravenous injection, but even oral, nasal, or anal administration is contemplated. In one embodiment, administration is by subcutaneous or intramuscular injection. To extend the time during which the disclosed polypeptides are available to stimulate a response, the polypeptide or nucleic acid encoding the polypeptide can be provided as an implant, an oily injection, or as a particulate system. The particulate system can be a microparticle, a microcapsule, a microsphere, a nanocapsule, or similar particle. (see, e.g., Banga, supra). A particulate carrier based on a synthetic polymer has been shown to act as an adjuvant to enhance the immune response, in addition to providing a controlled release. Aluminum salts can also be used as adjuvants to produce an immune response.

Optionally, one or more cytokines, such as interleukin (IL)-2, IL-6, IL-12, IL-15, RANTES, granulocyte macrophage colony stimulating factor (GM-CSF), tumor necrosis factor (TNF)-α, interferon (IFN)-α or IFN-γ, one or more growth factors, such as GM-CSF or G-CSF, one or more costimulatory molecules, such as ICAM-1, LFA-3, CD72, B7-1, B7-2, or other B7 related molecules; one or more molecules such as OX-40L or 41 BBL, or combinations of these molecules, can be used as biological adjuvants (see, for example, Salgaller et al., 1998, *J. Surg. Oncol.* 68(2): 122-38; Lotze et al., 2000, *Cancer J Sci. Am.* 6(Suppl 1):S61-6; Cao et al., 1998, *Stem Cells* 16(Suppl 1):251-60; Kuiper et al., 2000, *Adv. Exp. Med. Biol.* 465:381-90) with the disclosed immunogenic polypeptides. These molecules can be administered systemically (or locally) to the host. In several examples, IL-2, RANTES, GM-CSF, TNF-α, IFN-γ, G-CSF, LFA-3, CD72, B7-1, B7-2, B7-1 B.7-2, OX-40L, 41 BBL, and/or ICAM-1 are administered.

Pharmaceutical compositions including the disclosed polypeptides, and/or nucleic acids encoding the polypeptides are also disclosed herein. The pharmaceutical compositions can include one or more of pharmaceutically acceptable carriers, adjuvants (such as those described above), a stabilizing detergent (such as polysorbate 80 (TWEEN® 80) (Sorbitan-mono-9-octadecenoate-poly(oxy-1,2-ethanediyl); manufactured by ICI Americas, Wilmington, Del.), TWEEN® 40, TWEEN® 20, TWEEN® 60, ZWITTERGENT® 3-12, TEEPOL® HB7, and SPAN® 85 detergents, for example, in an amount of approximately 0.05 to 0.5%, such as at about 0.2%), a micelle-forming agent (such as PLURONIC® L62LF, L101, and L64 block copolymer, polyethylene glycol 1000, and TETRONIC® 1501, 150R1, 701, 901, 1301, and 130R1 block copolymer, for example, between 0.5 and 10%, or in an amount between 1.25 and 5%), and an oil (squalene, squalane, eicosane, tetratetracontane, glycerol, and peanut oil or other vegetable oils, for example, in an amount between 1 and 10%, or between 2.5 and 5%). In one embodiment, the pharmaceutical composition includes a mixture of stabilizing detergents, micelle-forming agent, and oil available under the name PROVAX® (IDEC Pharmaceuticals, San Diego, Calif.).

In some embodiments, a pharmaceutical composition includes one or more nucleic acids encoding a disclosed polypeptide. A therapeutically effective amount of the nucleic acid(s) can be administered to a subject in order to generate an immune response. In various embodiments, a nucleic acid encoding a biological adjuvant (such as those described above) can be cloned into same vector as a nucleic acid encoding a disclosed polypeptide, or the nucleic acid can be cloned into one or more separate vectors for co-administration. In addition, nonspecific immunomodulating factors such as Bacillus Calmette-Guerin (BCG) and levamisole can be co-administered.

One approach to administration of nucleic acids is direct immunization with plasmid DNA, such as with a mammalian expression plasmid. As described above, a nucleotide sequence encoding a disclosed polypeptide can be placed under the control of a promoter to increase expression of the molecule. Immunization by nucleic acid constructs is well known in the art and taught, for example, in U.S. Pat. No. 5,643,578 (which describes methods of immunizing vertebrates by introducing DNA encoding a desired antigen to elicit a cell-mediated or a humoral response), and U.S. Pat. No. 5,593,972 and U.S. Pat. No. 5,817,637 (which describe operably linking a nucleic acid sequence encoding an antigen to regulatory sequences enabling expression). U.S. Pat. No. 5,880,103 describes several methods of delivery of nucleic acids encoding immunogenic peptides or other antigens to an organism. The methods include liposomal delivery of the nucleic acids (or of the synthetic peptides themselves), and immune-stimulating constructs, or ISCOMs, negatively charged cage-like structures of 30-40 nm in size formed spontaneously on mixing cholesterol and Quil A™ (saponin).

In another approach to using nucleic acids for immunization, a disclosed immunogenic polypeptide can also be expressed by attenuated viral hosts or vectors or bacterial vectors. Recombinant vaccinia virus, adeno-associated virus (AAV), herpes virus, retrovirus, cytomegalovirus or other viral vectors (such as those described above) can be used to express the peptide or protein. For example, vaccinia vectors and methods useful in immunization protocols are described in U.S. Pat. No. 4,722,848. BCG (Bacillus Calmette Guerin)

provides another vector for expression of the peptides (see Stover, *Nature* 351:456-460, 1991).

In one embodiment, a nucleic acid encoding a disclosed immunogenic polypeptide is introduced directly into cells. For example, the nucleic acid can be loaded onto gold microspheres by standard methods and introduced into the skin by a device such as Bio-Rad's HELIOS™ Gene Gun. The nucleic acids can be "naked," consisting of plasmids under control of a strong promoter. Typically, the DNA is injected into muscle, although it can also be injected directly into other sites The amount of the disclosed immunogenic polypeptide, or nucleic acid molecule encoding the immunogenic polypeptide can vary depending upon the specific polypeptide(s), the route and protocol of administration, and the target population. In some embodiments, each dose includes about 1 µg to 1 mg of protein, such as from about 1 µg to about 500 µg, for example, from about 1 µg to about 100 µg, or about 1 µg to about 50 µg, such as about 1 µg, about 2 µg, about 5 µg, about 10 µg, about 15 µg, about 20 µg, about 25 µg, about 30 µg, about 40 µg, about 50 µg, about 75 µg, about 100 µg, about 200 µg, about 300 µg, about 400 µg, or about 500 µg. An optimal amount for a particular composition can be ascertained by standard studies involving observation of antibody titers and other responses in subjects (such as CTL or helper T cell responses).

The disclosed Env mosaic proteins (such as a set of three mosaic Env polypeptides) and/or nucleic acids encoding these proteins can be used in a multistep immunization regime. In some examples, the regime includes administering to a subject a therapeutically effective amount of a first immunogenic polypeptide (or mixture or set of immunogenic polypeptides) and boosting the immunogenic response with a second immunogenic polypeptide (or mixture or set of immunogenic polypeptides) after an appropriate period of time. This method of eliciting such an immune reaction is referred to as a "prime-boost" immunization regimen. Different dosages can be used in a series of sequential inoculations. Thus, a practitioner may administer a relatively large dose in a primary inoculation (prime) and then boost with relatively smaller doses. In some examples, the immunogenic polypeptide or mixture thereof administered in both the prime and boost inoculations are the same immunogenic polypeptide or mixture thereof. In other examples, the immunogenic polypeptide or mixture thereof administered in the boost is different from that administered in the prime inoculation.

The prime can be administered as a single dose or multiple doses, for example two doses, three doses, four doses, five doses, six doses, or more can be administered to a subject over days, weeks or months. The boost can be administered as a single dose or multiple doses, for example two to six doses or more can be administered to a subject over a day, a week or months. Multiple boosts can also be given, such one to five, or more. Different dosages can be used in a series of sequential inoculations. For example a relatively large dose in a primary inoculation and then a boost with relatively smaller doses. In some examples, there are weeks (for example, at least one week, at least 2 weeks, at least 3 weeks, at least 4 weeks, at least 6 weeks, at least 8 weeks, at least 12 weeks, at least 16 weeks, at least 24 weeks, or more) between administration of a prime and a boost or between administration of two boosts in a prime-boost regimen. The immune response against one or more of the Env mosaic proteins can be generated by one or more inoculations of a subject with an immunogenic composition disclosed herein.

The present disclosure is illustrated by the following non-limiting Examples.

EXAMPLES

Example 1

B Cell-Optimized Mosaic Design Strategy

This example describes the design strategy used to develop B cell-optimized mosaic Env proteins.

The B cell mosaic design was developed based on previous design strategies utilized for T cell mosaic polypeptides (Fischer et al., *Nature Med.* 13:100-106, 2007 and U.S. Pat. App. Publ. No. 2012/0231028, both of which are incorporated by reference herein in their entirety). The design strategy was modified as described below.

1. The capacity to incorporate structural information and alignments in the genetic algorithm for mosaic design (FIG. 1). Structural information was used in several ways in the design strategy. Alignments as input were required to associate a position in the alignment with a position on the structure. For every amino acid position in the alignment, the 10 amino acid positions that were closest to it based on the three-dimensional structure were defined, essentially defining a proximity sphere around every amino acid in the protein. The mosaic design code allows the user to define the dimensions of the proximity sphere by either choosing the number of the closest amino acids to be included, or by setting a spatially defined radius in angstroms; a 6.5 angstrom radius and a 10 amino acid maximum was used in the first designs. The positions in the proximity sphere were considered as a set, and all of the natural variation in each of those sets was determined, with the frequency of each form of the sphere calculated from the alignment. An additional constraint was added to the selection of recombinant mosaics—not only were breakpoints required to be spanned by sequences that are found in nature, but if a breakpoint occurred within a proximity sphere, it was also required that the new recombinant region be found in natural sequences. Co-optimization of the mosaic design to generate polypeptide sets that provide optimal coverage of spatially defined antibody epitope-sized regions became the selection criterion for the genetic algorithm. While most relevant B cell epitopes will be on the protein surface, including the constraint of finding common forms that are represented in nature in the internal part of the protein, essentially requiring no local violation of natural forms in terms of proximity spheres in any part of the structure, may help the mosaic constructs retain structural integrity.

2. A strategy for spanning hypervariable loop regions for the creation of an intact vaccine. HIV has four hypervariable regions within the variable loops V1, V2, V4, and V5 that typically evolve by insertion and deletion rather than just by base substitution. These short regions vary dramatically in length, charge, and number and location of N-linked glycosylation site motifs. They impact HIV neutralizing antibody recognition, and are essentially not alignable so could not be incorporated into part (1) above. Thus all hypervariable regions were excised from the alignments for the mosaic design phase, and if a position in the remaining core was close to these hypervariable regions, those positions were ignored during the mosaic design phase.

For the final designs, natural forms of these hypervariable regions that were short, relatively positively charged, with limited number of potential N-linked glycosylation sites (all desirable attributes in terms of antibody recognition based on neutralization data from large panels of antibodies compared to large panels of Envs tested in neutralization assays, provided by Dr. David Montefiori) were reintroduced. In addition, the frequencies of all peptide motifs of all lengths that were found within these regions were characterized, and natural variants with common motifs to span the hypervariable loops were favored.

3. A structural framework to define nearby regions in the protein. Ideally the HIV Env in its native form is needed, which requires a trimer structure. An early trimer model was used to enable the B cell mosaic design. The Env glycoprotein derived from a primary, neutralization-resistant (Tier 2) clade B isolate, HIV-1$_{JR-FL}$, was chosen for structural analysis. The gp120-gp41 proteolytic cleavage site in the HIV-1$_{JR-FL}$ Env was eliminated by two single-residue changes (R508S and R511S in standard HXB2 numbering). To improve the expression level on the cell surface, the gp41 cytoplasmic tail was truncated starting from Tyr 712. The modified Env, designated Env(-)ΔCT, thus contained the complete ectodomain and transmembrane regions, and was purified from the plasma membrane of Env-expressing cells after solubilization in Cymal-5 detergent. This procedure ensured that the purified membrane-anchored Env(-)ΔCT trimers were glycosylated and passed the quality-control checkpoints of the secretory pathway (Moulard & Decroly (2000) *Biochem. Biophys. Acta* 1469:121-132; Wyatt and Sodroski (1998) *Science* 280:1884-1888)) Importantly, HIV-1 Env(-)ΔCT complexes purified in this manner retain epitopes that are dependent upon conformation, glycosylation and quaternary structure. The detergent CYMAL®-5 was exchanged to CYMAL®-6 before preparation for cryo-EM imaging. The Env(-)ACT membrane glycoprotein, under the protection of CYMAL®-6, was flash-frozen on holey carbon film-coated EM grids and cryo-EM image data were collected at liquid nitrogen temperature. The imaging quality was found to be critically affected by the choice of the detergent and its concentration in the vitrified cryo-EM samples. A dataset of 90,306 single-particle images was assembled and subjected to multivariate data analysis, maximum-likelihood alignment and classification (Frank, J *Three-dimensional electron microscopy of macromolecular assemblies: visualization of biological molecules in their native state.* (Oxford Univ. Press, 2006); Sigworth (1998) *J. Struct. Biol.* 122:328-229; Scheres, et al. (2005) *J. Mol. Biol.* 348:139-149).

An initial model was generated by angular reconstitution from two-dimensional class averages refined by a maximum-likelihood approach (Sigworth et al. (1998) *J. Struct. Biol.* 122:328-339; Scheres et al. (2005) *J. Mol. Biol.* 348:139-149). The model was then further refined by a projection-matching algorithm to a final resolution of 10.8 Å, measured by Fourier shell correlation (FSC) with a 0.5-cutoff criterion (Liao & Frank (2010) *Structure* 18:768-775). Using the 10.8-Angstrom model as a reference, by analyzing a large dataset of 582,914 individual Env trimer images (equivalent to 1,748,742 protomers), a cryo-EM map was obtained that was estimated to have a resolution of ~6-Å based on the 0.5-cutoff of Fourier shell correlation. A reference model, obtained by filtering the ~6-Å reconstruction to 8-Å, was used to align a larger dataset of about 1-million single-particle images by projection matching. Tens of iterations of angular refinement yielded a reconstruction with an estimated resolution of ~4 Å by Fourier Shell Correlation 0.5-cutoff. The density map allowed an initial Cα model to be traced manually in the program O (Jones, T. A. (2004) *Acta Crystallogr. D* 60:211-2125) (FIG. 2). Interpretation of the Cα model was initially assisted by comparisons with crystal structures of the CD4-bound HIV-1 gp120 core, primary sequence information, secondary structure predictions by I-TASSER (Roy et al. (2010) *Nat. Protoc.* 5:725-738) and PHYRE (Kelley & Sternberg (2009) *Nat. Protoc.* 4:363-371), and known patterns of Env variation, glycosylation and disulfide bond formation.

Example 2

Env Mosaic Proteins

This example describes the design of Env mosaic proteins.

Using the strategies described in Example 1, structure-based Env mosaic proteins were designed. The design was first optimized based on restricting the design to a single HIV clade, a regional approach for Southern African vaccine (C clade). A multi-clade global vaccine design was also developed, one that used only Transmitted/Founder virus sequences and one that used the full database. The Env structural mosaic protein sequences for use in the initial testing phase are disclosed herein as SEQ ID NOs: 1-8. These proteins were stably expressed and could be bound by critical broadly neutralizing antibodies, and sCD4. In particular, they were designed for use as sets of three proteins, and for many of the antibodies tested, they showed differential affinity for the antibody (see Example 3), a trait considered desirable and consistent with the design strategy, in that each mosaic displays different but common epitope variants. The design was based on the hypothesis that exposure to the common epitope variants in a vaccine will elicit antibodies with greater breadth, and the proteins disclosed herein were contemplated to be used in combinations of three proteins. Theoretical analysis suggests that the main advantage of the B cell mosaic design would be the possibility of a global vaccine, rather than a within-clade mosaic improving single-clade regional vaccine over a set of three natural C clade Envs (FIG. 3). The other B cell mosaic advantage appears to be that they minimize the inclusion of rare and unique amino acids that could lead to type-specific response to a vaccine.

A total of eight proteins were designed, which can be used in combinations of three antigens for use in single polyvalent vaccine. Particular combinations are described below.

1. Within clade C: Cmos3.1 (SEQ ID NO: 1), Cmos3.2 (SEQ ID NO: 2), Cmos3.3 (SEQ ID NO: 3). This set is a mosaic trio that was optimized to maximize the coverage of C clade transmitted viruses from the CHAVI/CAVD SGA sequence collections. They were made serially, first optimizing the coverage of Cmos3.1; then fixing it, and optimizing for the addition of Cmos3.2; then fixing both 3.1 and 3.2 and adding Cmos3.3. The serial addition did not compromise the total coverage relative to optimizing the three at once, and has the advantage of having the potential to be used as a single, double or tri-valent vaccine.

2. Three clade trimer: Cmos3.1 (SEQ ID NO: 1)+Bmos3.1 (SEQ ID NO: 4)+CRF01mos3.1 (SEQ ID NO: 5). This combination uses the optimal single mosaic from the transmitted virus sequences from three clades. The coverage of each of these clades is very good, and they were designed from transmitted viruses, which may be advantageous. The coverage of other clades (A, G, F, CRF02, and others) was not optimal, but better than inter-clade coverage of with natural C clade antigens or C clade mosaics (FIG. 3). If transmitted virus input proves to be important, this may be a good way to get expanded coverage based on the available data.

3. Global mosaics: Mmos3.1 (SEQ ID NO: 6), Mmos3.2 (SEQ ID NO: 7), Mmos3.3 (SEQ ID NO: 8). There were not enough acute transmitted/founder sequences to give broad weight to some important epidemic lineages: clades A, G, F, and CRF01 and CRF02 are under-represented in the transmitted virus database, while B and C had a large enough sample size to work with. Thus chronic non-SGA sequences from the database were used to supplement the input data set for the under-represented lineages to create a global design. Thus this mosaic design set gives expanded coverage of all clades, but was not based on transmitted SGA sequences.

Example 3

Antigenicity Data

This example describes antigenicity of the global mosaic proteins described in Example 2.

The Mmos3.1, Mmos3.2, and Mmos3.3 polypeptides were expressed and tested in vitro using surface plasmon resonance (SPR). The dissociation constant of the polypeptides for various antibodies and epitopes was measured by SPR and is shown in Table 2. Low numbers represent antibodies with a slower off rates for the proteins. The antibodies names are listed on the left, the region of the HIV Env the target follows in parenthesis. CD4 is the receptor molecule on the HIV targeted T cell in natural infection. 17b is a monoclonal antibody that binds to the same region on the Env protein as the HIV-1 co-receptor molecule, and the capacity to bind to 17b and the co-receptor is CD4 inducible, hence the 17b (CD4i) nomenclature. The binding of CD4, and 17b after CD4 is bound, indicates that these proteins are well folded, and have native conformation in these regions, and the Env proteins undergo a biologically appropriate conformational change when CD4 is bound. The observation that these antibodies bind well to these proteins demonstrates that despite being artificial mosaic constructs, they form correctly folded proteins and retain the three-dimensional antigenic domains required for antibody binding.

TABLE 2

Antigenicity of B cell mosaic Envelopes using surface plasmon resonance

| Antibody/Epitope | Dissociation Constant Kd (nM) | | |
|---|---|---|---|
| | Mmos3.1 gp120 | Mmos3.2 gp120 | Mmos3.3 gp120 |
| CD4 | 14.0* | 2.9* | 8.4* |
| 17b (CD4i) | +++** | +++** | +++** |
| A32 (C1) | <1* | 0.2* | <1* |
| VRC01 (CD4 bs) | 5.7 | 19.1 | 3.4 |
| 19b (V3) | 3.3 | 32.7 | 8.4 |
| PG9 (V1-V2) | 339 | 8.5 | 369 |
| CH01 (V1-V2) | NB | NB | NB |
| 697D (V2) | 5.0 | 121 | 165 |
| 2G12 (—CHO) | 6.0 | 1543 | 412 |
| CH58 (V2) | NB | 59.8 | 14.4 |
| PGT128 | 4.6 | 5.3 | 3.7 |

*Kd from single-shot kinetics
**Relative to Con S gp140
NB = not bound

Each of the three polypeptides was titrated on PG9, a very potent HIV-specific neutralizing antibody that typically has high dissociation constants (FIGS. 4A-C). Mmos3.2 bound extremely well and the epitope exposure could trigger the B cell lineage. Mmos3.1 and Mmos3.3 are variants that are common in nature, but they did not bind PG9 as well as Mmos3.2. However, without being bound by theory, the presence of these variants in an immunogenic cocktail during affinity maturation could enable antibodies to evolve that bind well to each variant, tolerating the diversity (mimicking CH505). Mmos3.2 had a slow off rate for binding to PG9. RV144 A244 was one of the few gp120s that bind well to PG9 (40 nM). Mmos3.2 had a Kd of 8.5 nM (Table 1 and FIG. 4B), suggesting that the essential aspects of the epitope are present.

Binding of Mmos3.1, Mmos3.2, and Mmos3.3 to A32, sCD4, and T8 was tested (FIGS. 5-7). Each of the polypeptides was also titrated on HIV specific antibodies, including VRC01 (FIG. 8), 19*b* (FIG. 9), CH01 (FILG. 10), 697D (FIG. 11), 2G12 (FIG. 12), CH58 (FIG. 13), and PGT128 (FIGL. 14).

Example 4

Immunization of Animals

This example describes exemplary procedures for immunization of animals with the disclosed immunogenic polypeptides. Although particular methods are provided, one of ordinary skill in the art will appreciate that additional methods or variations of the described methods can also be utilized.

In some examples nucleic acid molecules encoding the disclosed immunogenic polypeptides are cloned into a plasmid or a viral vector (such as an adenoviral vector or a modified Ankara vaccinia virus vector). Study animals (for example, mice or monkeys) are administered plasmid or viral vector nucleic acid intramuscularly. Varying amounts of the nucleic acid can be administered, for example to test for an optimally effective amount.

In other examples nucleic acid molecules encoding the disclosed immunogenic polypeptides are cloned into an expression vector and expressed in a host cell. The polypeptides are purified using standard methods. Study animals (for example, mice or monkeys) are administered the polypeptides intramuscularly or subcutaneously. Varying doses are administered to determine optimal amounts for eliciting an immune response.

Immune responses elicited by the administered immunogenic polypeptides are assessed. For example, cellular immune responses are assessed using cytokine assays and/or interferon-γ ELISPOT assays. Humoral immune responses are assessed by direct ELISA utilizing one or more HIV proteins (such as a set of natural Env variants and/or the mosaic Env protein(s) administered to the animal). Neutralization assays (for example, a luciferase based pseudovirus neutralization assay) are also used to assess humoral immune responses.

Example 5

Treatment of HIV in a Subject

This example describes exemplary methods for treating or inhibiting an HIV infection in a subject, such as a human subject, by administration of one or more of the immunogenic polypeptides or one or more nucleic acids encoding the immunogenic polypeptides disclosed herein. Although particular methods, dosages and modes of administrations are provided, one skilled in the art will appreciate that variations can be made without substantially affecting the treatment.

Briefly, the method includes screening subjects to determine if they have HIV, such as HIV-1 or HIV-2. Subjects having HIV are selected for further treatment. In one example, subjects are selected who have increased levels of HIV antibodies in their blood, as detected with an enzyme-linked immunosorbent assay, Western blot, immunofluorescence assay or nucleic acid testing, including viral RNA or proviral DNA amplification methods. In one example, half of the subjects follow the established protocol for treatment of HIV (such as a highly active antiretroviral therapy). The other half follow the established protocol for treatment of HIV (such as treatment with highly active antiretroviral compounds) in combination with administration of the agents including a therapeutically effective amount of a disclosed immunogenic polypeptide that induces an immune response to HIV. However, pre-screening is not required prior to administration of the compositions disclosed herein.

In particular examples, the subject is treated prior to diagnosis of AIDS with the administration of a therapeutically effective amount of one or more of the disclosed immunogenic polypeptides. In some examples, the subject is treated with an established protocol for treatment of AIDS (such as a highly active antiretroviral therapy) prior to treatment with the administration of a therapeutic agent that includes one or more of the disclosed immunogenic polypeptides. However, such pre-treatment is not always required and can be determined by a skilled clinician.

Following selection, an effective amount of one or more (such as three) immunogenic polypeptides disclosed herein, or one or more (such as three) nucleic acids encoding disclosed immunogenic polypeptides is administered to the subject (such as an adult human or a newborn infant either at risk for contracting HIV or known to be infected with HIV). Additional agents, such as anti-viral agents, can also be administered to the subject simultaneously or prior to or following administration of the disclosed agents. Administration can be achieved by any method known in the art, such as oral, inhalation, intravenous, intramuscular, intraperitoneal, or subcutaneous administration.

The amount of the immunogenic polypeptides (or nucleic acids encoding the polypeptides) administered to prevent, reduce, inhibit, and/or treat HIV or a condition associated with it depends on the subject being treated, the severity of the disorder and the manner of administration of the immunogenic composition. Ideally, an effective amount of the immunogenic composition is an amount sufficient to prevent, reduce, and/or inhibit, and/or treat the condition (for example, HIV) in a subject without causing a substantial cytotoxic effect in the subject. An effective amount can be readily determined by one skilled in the art, for example using routine trials establishing dose response curves. In addition, particular exemplary dosages are provided above. The therapeutic compositions can be administered in a single dose delivery, via continuous delivery over an extended time period, in a repeated administration protocol (for example, by a daily, weekly or monthly repeated administration protocol). In one example, a therapeutically effective amount of a disclosed antigen that induces an immune response to HIV is administered intravenously or intramuscularly to a human. As such, these compositions may be formulated with an inert diluent or with a pharmaceutically acceptable carrier. Immunogenic compositions can be taken long term (for example over a period of months or years).

Following the administration of one or more therapies, subjects having HIV (for example, HIV-1 or HIV-2) can be monitored for reductions in HIV levels, increases in a subjects CD4+ T cell count or reductions in one or more clinical symptoms associated with HIV infection. In particular examples, subjects are analyzed one or more times, starting 7 days following treatment. Subjects can be monitored using any method known in the art. For example, biological samples from the subject, including blood, can be obtained and alterations in HIV or CD4+ T cell levels evaluated.

In particular examples, if subjects are stable or have a minor, mixed or partial response to treatment, they can be re-treated after re-evaluation with the same or a different schedule and/or preparation of agents that they previously received for the desired amount of time, including the duration of a subject's lifetime. A partial response is a reduction, such as at least a 10%, at least 20%, at least 30%, at least 40%, at least 50% or at least 70% reduction of HIV viral load, HIV replication or combination thereof. A partial response may also be an increase in CD4+ T cell count such as at least 350 T cells per microliter.

Example 6

Treatment of Subjects

This example describes methods that can be used to treat a subject that has or is at risk of having an infection from HIV that can be treated by eliciting an immune response, such as a neutralizing antibody response to HIV.

In particular examples, the method includes screening a subject having, thought to have or at risk of having a HIV infection. Subjects of an unknown infection status can be examined to determine if they have an infection, for example using serological tests, physical examination, enzyme-linked immunosorbent assay (ELISA), radiological screening, or other diagnostic techniques known to those of skill in the art. In some examples, subjects are screened to identify a HIV infection, with a serological test, or with a nucleic acid probe specific for a HIV nucleic acid. Subjects found to (or known to) have a HIV infection can be administered one or more disclosed immunogenic polypeptides (or nucleic acids encoding the polypeptides). Subjects may also be selected who are at risk of developing HIV for example, subjects exposed to HIV.

Subjects selected for treatment can be administered an effective amount of the disclosed immunogenic polypeptides or nucleic acids encoding the disclosed immunogenic polypeptides. The particular dose can be determined by a skilled clinician. The polypeptides (or nucleic acids) can be administered in one or several doses, for example continuously, daily, weekly, or monthly. When administered sequentially the time separating the administration of the doses of the immunogenic polypeptides can be seconds, minutes, hours, days, or even weeks.

Subjects are periodically tested for presence of HIV or HIV antibodies in their blood, as detected with an enzyme-linked immunosorbent assay, Western blot, immunofluorescence assay or nucleic acid testing, including viral RNA or proviral DNA amplification methods.

In view of the many possible embodiments to which the principles of the disclosure may be applied, it should be recognized that the illustrated embodiments are only examples and should not be taken as limiting the scope of the invention. Rather, the scope of the invention is defined by the following claims. We therefore claim as our invention all that comes within the scope and spirit of these claims.

We claim:

1. A set of isolated immunogenic polypeptides comprising:
   polypeptides comprising the amino acid sequences set forth as SEQ ID NO: 1, SEQ ID NO: 2, and SEQ ID NO: 3;
   polypeptides comprising the amino acid sequences set forth as SEQ ID NO: 1, SEQ ID NO: 4, and SEQ ID NO: 5; or
   polypeptides comprising the amino acid sequences set forth as SEQ ID NO: 6, SEQ ID NO: 7, and SEQ ID NO: 8.

2. An isolated immunogenic polypeptide comprising the amino acid sequence set forth as any one of SEQ ID NOs: 1-8 or an amino acid sequence having at least 95% identity to the amino acid sequence set forth as any one of SEQ ID NOs: 1-8.

3. The isolated immunogenic polypeptide of claim 2, wherein the polypeptide consists of the amino acid sequence set forth as any one of SEQ ID NOs: 1-8.

4. A set of isolated immunogenic polypeptides comprising two or more of the polypeptides of claim 2.

5. The set of isolated immunogenic polypeptides of claim 4, wherein the two or more polypeptides are selected from polypeptides consisting of the amino acid sequences set forth as any one of SEQ ID NOs: 1-8.

6. A pharmaceutical composition comprising:
   one or more of the isolated immunogenic polypeptides of claim 2; and
   a pharmaceutically acceptable carrier.

7. The pharmaceutical composition of claim 6, further comprising one or more of an adjuvant, a detergent, a micelle-forming agent, and an oil.

8. A pharmaceutical composition comprising:
   the set of immunogenic polypeptides of claim 4; and
   a pharmaceutically acceptable carrier.

9. A method for eliciting an immune response to human immunodeficiency virus (HIV) in a subject, comprising administering to the subject an effective amount of:
   the set of immunogenic polypeptides of claim 4;
   thereby eliciting an immune response to HIV in the subject.

10. The method of claim 9, wherein the polypeptides in the set are administered to the subject simultaneously, substantially simultaneously, or sequentially.

11. The method of claim 9, further comprising administering to the subject a therapeutically effective amount of an anti-viral agent.

12. A method for eliciting an immune response to human immunodeficiency virus (HIV) in a subject, comprising administering to the subject an effective amount of the set of immunogenic polypeptides of claim 1, thereby eliciting an immune response to HIV in the subject.

13. A method for eliciting an immune response to human immunodeficiency virus (HIV) in a subject, comprising administering to the subject an effective amount of the immunogenic polypeptide of claim 2, thereby eliciting an immune response to HIV in the subject.

* * * * *

SEQUENCE LISTING

<160> NUMBER OF SEQ ID NOS: 9

<210> SEQ ID NO 1
<211> LENGTH: 854
<212> TYPE: PRT
<213> ORGANISM: Artificial Sequence
<220> FEATURE:
<223> OTHER INFORMATION: Cmos3.1 mosaic protein

<400> SEQUENCE: 1

```
Met Arg Val Arg Gly Ile Leu Arg Asn Tyr Gln Gln Trp Trp Ile Trp
1               5                   10                  15

Gly Ile Leu Gly Phe Trp Met Leu Met Ile Cys Ser Val Val Gly Asn
            20                  25                  30

Leu Trp Val Thr Val Tyr Tyr Gly Val Pro Val Trp Lys Glu Ala Lys
        35                  40                  45

Thr Thr Leu Phe Cys Ala Ser Asp Ala Lys Ala Tyr Glu Lys Glu Val
50                  55                  60

His Asn Val Trp Ala Thr His Ala Cys Val Pro Thr Asp Pro Asn Pro
65                  70                  75                  80

Gln Glu Met Val Leu Glu Asn Val Thr Glu Asn Phe Asn Met Trp Lys
                85                  90                  95

Asn Asp Met Val Asp Gln Met His Glu Asp Ile Ile Ser Leu Trp Asp
            100                 105                 110

Gln Ser Leu Lys Pro Cys Val Lys Leu Thr Pro Leu Cys Val Thr Leu
        115                 120                 125

Asn Cys Ser Thr Ala Thr Asn Thr Thr Thr Arg Asn Asn Thr Val Gly
130                 135                 140

Glu Glu Ile Lys Asn Cys Ser Phe Asn Ile Thr Thr Glu Ile Arg Asp
145                 150                 155                 160

Lys Lys Lys Asn Val Tyr Ala Leu Phe Tyr Lys Leu Asp Ile Val Pro
                165                 170                 175

Leu His Glu Lys Asp Asn Asn Ile Ser Tyr Arg Leu Ile Asn Cys Asn
            180                 185                 190

Thr Ser Thr Ile Thr Gln Ala Cys Pro Lys Val Ser Phe Asp Pro Ile
        195                 200                 205

Pro Ile His Tyr Cys Ala Pro Ala Gly Tyr Ala Ile Leu Lys Cys Asn
210                 215                 220

Asn Lys Thr Phe Asn Gly Thr Gly Pro Cys Asn Asn Val Ser Thr Val
225                 230                 235                 240

Gln Cys Thr His Gly Ile Lys Pro Val Val Ser Thr Gln Leu Leu Leu
                245                 250                 255

Asn Gly Ser Leu Ala Glu Glu Ile Ile Ile Arg Ser Glu Asn Leu
            260                 265                 270

Thr Asn Asn Ala Lys Thr Ile Ile Val His Leu Lys Glu Pro Val Glu
        275                 280                 285

Ile Val Cys Thr Arg Pro Asn Asn Asn Thr Arg Lys Ser Ile Arg Ile
290                 295                 300

Gly Pro Gly Gln Thr Phe Tyr Ala Thr Gly Asp Ile Ile Gly Asp Ile
305                 310                 315                 320

Arg Gln Ala His Cys Asn Val Ser Lys Gln Asn Trp Asn Arg Thr Leu
                325                 330                 335

Gln Gln Val Gly Arg Lys Leu Ala Glu His Phe Pro Asn Arg Asn Ile
            340                 345                 350

Thr Phe Asn His Ser Ser Gly Gly Asp Leu Glu Ile Thr Thr His Ser
```

```
                355                 360                 365
    Phe Asn Cys Arg Gly Glu Phe Phe Tyr Cys Asn Thr Ser Gly Leu Phe
        370                 375                 380

Asn Gly Thr Tyr His Pro Asn Gly Thr Tyr Asn Glu Thr Ala Val Asn
385                 390                 395                 400

Ser Ser Asp Thr Ile Thr Leu Gln Cys Arg Ile Lys Gln Ile Ile Asn
                    405                 410                 415

Met Trp Gln Gly Val Gly Arg Ala Met Tyr Ala Pro Pro Ile Glu Gly
                420                 425                 430

Asn Ile Thr Cys Lys Ser Asn Ile Thr Gly Leu Leu Leu Thr Arg Asp
                    435                 440                 445

Gly Gly Lys Asn Asn Ser Gly Pro Glu Thr Phe Arg Pro Gly Gly Gly
                450                 455                 460

Asp Met Arg Asp Asn Trp Arg Ser Glu Leu Tyr Lys Tyr Lys Val Val
465                 470                 475                 480

Glu Ile Lys Pro Leu Gly Ile Ala Pro Thr Lys Ala Lys Arg Arg Val
                    485                 490                 495

Val Glu Arg Glu Lys Arg Ala Val Gly Ile Gly Ala Val Phe Leu Gly
                500                 505                 510

Phe Leu Gly Ala Ala Gly Ser Thr Met Gly Ala Ala Ser Ile Thr Leu
                515                 520                 525

Thr Val Gln Ala Arg Gln Leu Leu Ser Gly Ile Val Gln Gln Gln Ser
                530                 535                 540

Asn Leu Leu Arg Ala Ile Glu Ala Gln Gln His Met Leu Gln Leu Thr
545                 550                 555                 560

Val Trp Gly Ile Lys Gln Leu Gln Ala Arg Val Leu Ala Ile Glu Arg
                    565                 570                 575

Tyr Leu Lys Asp Gln Gln Leu Leu Gly Ile Trp Gly Cys Ser Gly Lys
                580                 585                 590

Leu Ile Cys Thr Thr Ala Val Pro Trp Asn Ser Ser Trp Ser Asn Lys
                    595                 600                 605

Ser Gln Gly Glu Ile Trp Gly Asn Met Thr Trp Met Gln Trp Asp Arg
                610                 615                 620

Glu Ile Ser Asn Tyr Thr Asn Thr Ile Tyr Arg Leu Leu Glu Asp Ser
625                 630                 635                 640

Gln Ile Gln Gln Glu Lys Asn Glu Lys Asp Leu Leu Ala Leu Asp Ser
                    645                 650                 655

Trp Lys Asn Leu Trp Ser Trp Phe Ser Ile Thr Asn Trp Leu Trp Tyr
                660                 665                 670

Ile Lys Ile Phe Ile Met Ile Val Gly Gly Leu Ile Gly Leu Arg Ile
                    675                 680                 685

Ile Phe Ala Val Leu Ser Ile Val Asn Arg Val Arg Gln Gly Tyr Ser
                690                 695                 700

Pro Leu Ser Phe Gln Thr Leu Ile Pro Asn Pro Arg Gly Pro Asp Arg
705                 710                 715                 720

Leu Gly Arg Ile Glu Glu Gly Gly Glu Gln Asp Arg Asp Arg Ser
                    725                 730                 735

Ile Arg Leu Val Asn Gly Phe Leu Ala Leu Ala Trp Asp Asp Leu Arg
                740                 745                 750

Ser Leu Cys Leu Phe Ser Tyr His Arg Leu Arg Asp Phe Ile Leu Ile
                    755                 760                 765

Ala Ala Arg Ala Val Glu Leu Leu Gly Arg Ser Ser Leu Arg Gly Leu
                770                 775                 780
```

Gln Arg Gly Trp Glu Ala Leu Lys Tyr Leu Gly Ser Leu Val Gln Tyr
785                 790                 795                 800

Trp Gly Leu Glu Leu Lys Lys Ser Ala Ile Ser Leu Leu Asp Thr Ile
            805                 810                 815

Ala Ile Ala Val Ala Glu Gly Thr Asp Arg Ile Ile Gly Val Val Gln
        820                 825                 830

Arg Ile Cys Arg Ala Ile Arg Asn Ile Pro Arg Arg Ile Arg Gln Gly
            835                 840                 845

Phe Glu Ala Ala Leu Gln
        850

<210> SEQ ID NO 2
<211> LENGTH: 843
<212> TYPE: PRT
<213> ORGANISM: Artificial Sequence
<220> FEATURE:
<223> OTHER INFORMATION: Cmos3.2 mosaic protein

<400> SEQUENCE: 2

Met Arg Val Met Gly Ile Leu Arg Asn Cys Gln Gln Trp Trp Ile Trp
1               5                   10                  15

Ser Ile Leu Gly Phe Trp Met Leu Met Ile Cys Asn Val Met Gly Asn
            20                  25                  30

Leu Trp Val Thr Val Tyr Tyr Gly Val Pro Val Trp Arg Glu Ala Lys
        35                  40                  45

Thr Thr Leu Phe Cys Ala Ser Asp Ala Lys Ala Tyr Glu Arg Glu Val
    50                  55                  60

His Asn Val Trp Ala Thr His Ala Cys Val Pro Thr Asp Pro Ser Pro
65                  70                  75                  80

Gln Glu Ile Val Leu Glu Asn Val Thr Glu Asn Phe Asn Met Trp Lys
                85                  90                  95

Asn Asp Met Val Asp Gln Met His Glu Asp Val Ile Ser Leu Trp Asp
            100                 105                 110

Glu Ser Leu Lys Pro Cys Val Lys Leu Thr Pro Leu Cys Val Thr Leu
        115                 120                 125

Asn Cys Thr Glu Val Ala Lys Ala Thr Gly Asn Phe Thr Gly Val Glu
    130                 135                 140

Met Lys Asn Cys Ser Phe Asn Thr Thr Thr Glu Leu Arg Asp Lys Lys
145                 150                 155                 160

Glu Asn Gln Tyr Ala Leu Phe Tyr Arg Leu Asp Ile Val Pro Leu Ser
                165                 170                 175

Lys Lys Asp Lys Thr Asn Asn Asp Ser Gly Glu Tyr Ile Leu Ile Asn
            180                 185                 190

Cys Asn Thr Ser Ala Ile Thr Gln Ala Cys Pro Lys Val Thr Phe Asp
        195                 200                 205

Pro Ile Pro Ile His Tyr Cys Thr Pro Ala Gly Tyr Ala Ile Leu Lys
    210                 215                 220

Cys Lys Asp Lys Thr Phe Asn Gly Thr Gly Pro Cys Arg Asn Val Ser
225                 230                 235                 240

Thr Val Gln Cys Thr His Gly Ile Lys Pro Val Val Ser Thr Gln Leu
                245                 250                 255

Leu Leu Asn Gly Ser Leu Ala Glu Glu Glu Ile Ile Ile Arg Ser Glu
            260                 265                 270

Asn Leu Thr Asp Asn Val Lys Thr Ile Ile Val His Leu Asn Glu Ser
        275                 280                 285

```
Val Glu Ile Val Cys Thr Arg Pro Gly Asn Asn Thr Arg Lys Ser Val
290                 295                 300

Arg Ile Gly Pro Gly Gln Ala Phe Tyr Ala Thr Gly Asp Ile Ile Gly
305                 310                 315                 320

Asp Ile Arg Glu Ala His Cys Asn Ile Ser Arg Trp Ser Glu Thr Leu
            325                 330                 335

Glu Lys Val Arg Glu Lys Leu Lys Gly Leu Phe Asn Lys Thr Ile Glu
            340                 345                 350

Phe Asn Ser Ser Ser Gly Gly Asp Leu Glu Ile Thr Thr His Ser Phe
        355                 360                 365

Asn Cys Arg Gly Glu Phe Phe Tyr Cys Asn Thr Ser Lys Leu Trp Ser
370                 375                 380

Asn Glu Ser Asn Asp Gly Asn Asp Thr Ile Ile Leu Pro Cys Arg Ile
385                 390                 395                 400

Lys Gln Ile Ile Asn Met Trp Gln Glu Val Gly Arg Ala Met Tyr Ala
                405                 410                 415

Pro Pro Ile Ala Gly Ser Ile Thr Cys Lys Ser Ser Ile Thr Gly Leu
            420                 425                 430

Leu Leu Val Arg Asp Gly Gly Ile Thr Asn Asn Thr Glu Thr Phe
            435                 440                 445

Arg Pro Gly Gly Gly Asn Met Lys Asp Asn Trp Arg Ser Glu Leu Tyr
450                 455                 460

Lys Tyr Lys Val Val Glu Ile Gln Pro Leu Gly Val Ala Pro Thr Gly
465                 470                 475                 480

Ala Lys Arg Arg Val Val Glu Arg Glu Lys Arg Ala Val Gly Ile Gly
                485                 490                 495

Ala Val Phe Leu Gly Phe Leu Gly Ala Ala Gly Ser Thr Met Gly Ala
            500                 505                 510

Ala Ser Ile Thr Leu Thr Val Gln Ala Arg Gln Leu Leu Ser Gly Ile
        515                 520                 525

Val Gln Gln Gln Ser Asn Leu Leu Lys Ala Ile Glu Ala Gln Gln His
530                 535                 540

Met Leu Gln Leu Thr Val Trp Gly Ile Lys Gln Leu Gln Thr Arg Val
545                 550                 555                 560

Leu Ala Ile Glu Arg Tyr Leu Lys Asp Gln Gln Leu Leu Gly Leu Trp
                565                 570                 575

Gly Cys Ser Gly Lys Leu Ile Cys Thr Thr Asn Val Pro Trp Asn Ser
            580                 585                 590

Ser Trp Ser Asn Lys Ser Gln Thr Asp Ile Trp Asp Asn Met Thr Trp
        595                 600                 605

Ile Gln Trp Asp Arg Glu Ile Ser Asn Tyr Ser Asn Thr Ile Tyr Lys
610                 615                 620

Leu Leu Glu Asp Ser Gln Asn Gln Gln Glu Gln Asn Glu Lys Asp Leu
625                 630                 635                 640

Leu Ala Leu Asp Ser Trp Asn Asn Leu Trp Asn Trp Phe Asp Ile Thr
                645                 650                 655

Lys Trp Leu Trp Tyr Ile Lys Ile Phe Ile Ile Val Gly Gly Leu
            660                 665                 670

Ile Gly Leu Arg Ile Ile Leu Gly Val Leu Ser Ile Val Lys Arg Val
        675                 680                 685

Arg Gln Gly Tyr Ser Pro Leu Ser Phe Gln Thr Leu Thr Pro Asn Pro
690                 695                 700
```

```
Arg Gly Leu Asp Arg Leu Gly Arg Ile Glu Glu Gly Gly Glu Gln
705                 710                 715                 720

Asp Lys Asp Arg Ser Ile Arg Leu Val Ser Gly Phe Leu Ala Leu Ala
            725                 730                 735

Trp Glu Asp Leu Arg Asn Leu Cys Leu Phe Ser Tyr His Gln Leu Arg
            740                 745                 750

Asp Phe Ile Leu Ile Val Ala Arg Ala Val Glu Leu Leu Gly Arg Ser
            755                 760                 765

Ser Leu Arg Gly Leu Gln Lys Gly Trp Glu Ala Leu Lys Tyr Leu Gly
            770                 775                 780

Asn Leu Val Gln Tyr Trp Gly Leu Glu Ile Lys Lys Ser Ala Ile Asn
785                 790                 795                 800

Leu Leu Asp Thr Thr Ala Ile Ala Val Ala Glu Gly Thr Asp Arg Ile
            805                 810                 815

Ile Glu Leu Ile Gln Arg Ile Cys Arg Ala Ile Cys Asn Ile Pro Thr
            820                 825                 830

Arg Ile Arg Gln Gly Phe Glu Ala Ala Leu Leu
            835                 840

<210> SEQ ID NO 3
<211> LENGTH: 848
<212> TYPE: PRT
<213> ORGANISM: Artificial Sequence
<220> FEATURE:
<223> OTHER INFORMATION: Cmos3.3 mosaic protein

<400> SEQUENCE: 3

Met Arg Val Arg Gly Ile Gln Arg Asn Trp Pro Gln Trp Trp Ile Trp
1               5                   10                  15

Gly Ile Leu Gly Phe Trp Met Ile Ile Cys Arg Gly Val Gly Asn
            20                  25                  30

Leu Trp Val Thr Val Tyr Tyr Gly Val Pro Val Trp Lys Glu Ala Lys
            35                  40                  45

Ala Thr Leu Phe Cys Ala Ser Asp Ala Lys Ala Tyr Glu Arg Glu Val
50                  55                  60

His Asn Ile Trp Ala Thr His Ala Cys Val Pro Thr Asp Pro Asn Pro
65                  70                  75                  80

Gln Glu Leu Val Leu Glu Asn Val Thr Glu Asn Phe Asn Met Trp Glu
            85                  90                  95

Asn Asp Met Val Asp Gln Met His Gln Asp Val Ile Ser Leu Trp Asp
            100                 105                 110

Gln Ser Leu Lys Pro Cys Val Lys Leu Thr Pro Leu Cys Val Thr Leu
            115                 120                 125

Asn Cys Ser Asn Val Asn Ser Asn Arg Thr Val Asp Asn Ala Thr Gln
130                 135                 140

Gly Glu Met Lys Asn Cys Ser Phe Asn Met Thr Thr Glu Leu Arg Asp
145                 150                 155                 160

Lys Lys Arg Gln Val Tyr Ala Leu Phe Tyr Lys Leu Asp Ile Val Pro
            165                 170                 175

Ile Asn Glu Ser Ser Ser Ser Glu Tyr Arg Leu Ile Asn Cys Asn
            180                 185                 190

Thr Ser Ala Ile Ala Gln Ala Cys Pro Lys Val Ser Phe Glu Pro Ile
            195                 200                 205

Pro Ile His Tyr Cys Ala Pro Ala Gly Tyr Ala Ile Leu Lys Cys Asn
            210                 215                 220
```

-continued

```
Asn Lys Thr Phe Asn Gly Thr Gly Pro Cys Thr Asn Val Ser Thr Val
225                 230                 235                 240

Gln Cys Thr His Gly Ile Arg Pro Val Val Ser Thr Gln Leu Leu Leu
            245                 250                 255

Asn Gly Ser Leu Ala Glu Gln Glu Ile Val Ile Arg Ser Glu Asn Leu
        260                 265                 270

Thr Asp Asn Ala Lys Ile Ile Ile Val Gln Leu Asn Lys Ser Val Glu
    275                 280                 285

Ile Asn Cys Thr Arg Pro Asn Asn Thr Arg Thr Ser Ile Arg Ile
290                 295                 300

Gly Pro Gly Gln Ala Phe Tyr Ala Thr Asn Gly Ile Ile Gly Asp Ile
305                 310                 315                 320

Arg Gln Ala His Cys Asn Ile Ser Arg Glu Leu Trp Asn Lys Thr Leu
                325                 330                 335

Glu Gly Val Arg Glu Lys Leu Lys Glu His Phe Pro Asn Arg Thr Ile
            340                 345                 350

Asn Phe Asn Gln Ser Ser Gly Gly Asp Leu Glu Ile Thr Thr His Ser
        355                 360                 365

Phe Asn Cys Arg Gly Glu Phe Phe Tyr Cys Asn Thr Ser Gly Leu Phe
    370                 375                 380

Lys Asn Asn Leu Thr Ala Ser Asn Thr Glu Ser Asn Gln Thr Ile Thr
385                 390                 395                 400

Leu Pro Cys Arg Ile Lys Gln Ile Ile Asn Met Trp Gln Gly Val Gly
                405                 410                 415

Arg Ala Met Tyr Ala Pro Pro Ile Ala Gly Asn Ile Thr Cys Lys Ser
            420                 425                 430

Asn Ile Thr Gly Leu Leu Leu Thr Arg Asp Gly Gly Thr Asn Asp Ser
        435                 440                 445

Met Thr Glu Thr Phe Arg Pro Gly Gly Gly Asn Met Lys Asp Asn Trp
    450                 455                 460

Arg Ser Glu Leu Tyr Lys Tyr Lys Val Val Glu Ile Lys Pro Leu Gly
465                 470                 475                 480

Val Ala Pro Thr Glu Ala Lys Arg Arg Val Val Glu Arg Glu Lys Arg
                485                 490                 495

Ala Val Gly Leu Gly Ala Val Phe Leu Gly Phe Leu Gly Ala Ala Gly
            500                 505                 510

Ser Thr Met Gly Ala Ala Ser Ile Thr Leu Thr Val Gln Ala Arg Gln
        515                 520                 525

Leu Leu Ser Gly Ile Val Gln Gln Gln Asn Asn Leu Leu Arg Ala Ile
    530                 535                 540

Glu Ala Gln Gln His Met Leu Gln Leu Thr Val Trp Gly Ile Lys Gln
545                 550                 555                 560

Leu Gln Ala Arg Val Leu Ala Leu Glu Arg Tyr Leu Gln Asp Gln Gln
                565                 570                 575

Leu Leu Gly Ile Trp Gly Cys Ser Gly Lys Leu Ile Cys Thr Thr Asn
            580                 585                 590

Val Pro Trp Asn Ser Ser Trp Ser Asn Lys Thr Gln Asp Glu Ile Trp
        595                 600                 605

Gly Asn Met Thr Trp Met Gln Trp Glu Lys Glu Ile Ser Asn Tyr Thr
    610                 615                 620

Asp Thr Ile Tyr Arg Leu Leu Glu Glu Ser Gln Thr Gln Gln Glu Gln
625                 630                 635                 640

Asn Glu Lys Asp Leu Leu Ala Leu Asp Lys Trp Gln Asn Leu Trp Ser
```

```
                    645                 650                 655
Trp Phe Asn Ile Thr Asn Trp Leu Trp Tyr Ile Lys Ile Phe Ile Met
                660                 665                 670

Ile Val Gly Gly Leu Ile Gly Leu Arg Ile Ile Phe Ala Val Leu Ser
                675                 680                 685

Ile Val Asn Arg Val Arg Gln Gly Tyr Ser Pro Leu Ser Phe Gln Thr
                690                 695                 700

Leu Ile Pro Ser Pro Arg Gly Pro Asp Arg Leu Gly Gly Ile Glu Glu
705                 710                 715                 720

Glu Gly Gly Glu Gln Asp Arg Asp Arg Ser Val Arg Leu Val Ser Gly
                725                 730                 735

Phe Leu Ser Leu Ala Trp Asp Asp Leu Arg Ser Leu Cys Leu Phe Cys
                740                 745                 750

Tyr His Arg Leu Arg Asp Phe Ile Leu Ile Ala Ala Arg Ala Ala Glu
                755                 760                 765

Leu Leu Gly Arg Ser Ser Leu Lys Gly Leu Gln Arg Gly Trp Glu Ile
                770                 775                 780

Leu Lys Tyr Leu Gly Asn Leu Leu Gln Tyr Trp Gly Leu Glu Leu Lys
785                 790                 795                 800

Arg Ser Ala Ile Ser Leu Leu Asp Thr Thr Ala Ile Thr Val Ala Glu
                805                 810                 815

Gly Thr Asp Arg Ile Ile Glu Ile Val Gln Arg Ile Cys Arg Ala Ile
                820                 825                 830

Cys Asn Ile Pro Arg Arg Ile Arg Gln Gly Phe Glu Thr Ala Leu Leu
                835                 840                 845

<210> SEQ ID NO 4
<211> LENGTH: 850
<212> TYPE: PRT
<213> ORGANISM: Artificial Sequence
<220> FEATURE:
<223> OTHER INFORMATION: Bmos3.1 mosaic protein

<400> SEQUENCE: 4

Met Arg Val Lys Gly Ile Arg Lys Asn Tyr Gln His Leu Trp Arg Trp
1               5                   10                  15

Gly Thr Met Leu Leu Gly Met Leu Met Ile Cys Ser Ala Ala Glu Gln
                20                  25                  30

Leu Trp Val Thr Val Tyr Tyr Gly Val Pro Val Trp Lys Glu Ala Thr
                35                  40                  45

Thr Thr Leu Phe Cys Ala Ser Asp Ala Lys Ala Tyr Asp Thr Glu Val
            50                  55                  60

His Asn Val Trp Ala Thr His Ala Cys Val Pro Thr Asp Pro Asn Pro
65                  70                  75                  80

Gln Glu Val Val Leu Glu Asn Val Thr Glu Asn Phe Asn Met Trp Lys
                85                  90                  95

Asn Asn Met Val Glu Gln Met His Glu Asp Ile Ile Ser Leu Trp Asp
                100                 105                 110

Gln Ser Leu Lys Pro Cys Val Lys Leu Thr Pro Leu Cys Val Thr Leu
                115                 120                 125

Asn Cys Thr Asp Val Ser Ser Asn Ser Thr Ser Val Asn Ile Thr Ser
            130                 135                 140

Glu Lys Gly Glu Ile Lys Asn Cys Ser Phe Asn Ile Thr Thr Ser Ile
145                 150                 155                 160

Arg Gly Lys Met Gln Lys Glu Tyr Ala Leu Phe Tyr Lys Leu Asp Ile
```

```
            165                 170                 175
Val Pro Ile Asp Asn Asp Asn Arg Asn Ser Tyr Arg Leu Ile Ser
            180                 185                 190

Cys Asn Thr Ser Val Ile Thr Gln Ala Cys Pro Lys Val Ser Phe Glu
        195                 200                 205

Pro Ile Pro Ile His Tyr Cys Ala Pro Ala Gly Phe Ala Ile Leu Lys
        210                 215                 220

Cys Asn Asp Lys Lys Phe Asn Gly Thr Gly Pro Cys Lys Asn Val Ser
225                 230                 235                 240

Thr Val Gln Cys Thr His Gly Ile Arg Pro Val Val Ser Thr Gln Leu
            245                 250                 255

Leu Leu Asn Gly Ser Leu Ala Glu Glu Val Val Ile Arg Ser Glu
        260                 265                 270

Asn Phe Thr Asn Asn Ala Lys Ile Ile Val Gln Leu Asn Glu Ser
        275                 280                 285

Val Val Ile Asn Cys Thr Arg Pro Asn Asn Thr Arg Lys Ser Ile
        290                 295                 300

His Ile Gly Pro Gly Arg Ala Phe Tyr Ala Thr Gly Glu Ile Ile Gly
305                 310                 315                 320

Asp Ile Arg Gln Ala His Cys Asn Leu Ser Arg Thr His Trp Asn Asn
                325                 330                 335

Thr Leu Lys Gln Ile Val Ile Lys Leu Arg Glu Gln Phe Gly Asn Lys
            340                 345                 350

Thr Ile Val Phe Asn Gln Ser Ser Gly Gly Asp Pro Glu Ile Val Met
            355                 360                 365

His Ser Phe Asn Cys Gly Gly Glu Phe Phe Tyr Cys Asn Thr Thr Gln
        370                 375                 380

Leu Phe Asn Ser Thr Trp Asn Arg Asn Asp Thr Trp Asn Asp Thr Trp
385                 390                 395                 400

Lys Asp Thr Thr Asn Asp Asn Ile Thr Leu Pro Cys Arg Ile Lys Gln
                405                 410                 415

Ile Ile Asn Met Trp Gln Glu Val Gly Lys Ala Met Tyr Ala Pro Pro
            420                 425                 430

Ile Arg Gly Gln Ile Arg Cys Ser Ser Asn Ile Thr Gly Leu Leu Leu
        435                 440                 445

Thr Arg Asp Gly Gly Asn Ser Ser Ser Asn Asn Glu Thr Phe Arg Pro
        450                 455                 460

Gly Gly Gly Asp Met Arg Asp Asn Trp Arg Ser Glu Leu Tyr Lys Tyr
465                 470                 475                 480

Lys Val Val Lys Ile Glu Pro Leu Gly Val Ala Pro Thr Lys Ala Lys
                485                 490                 495

Arg Arg Val Val Gln Arg Glu Lys Arg Ala Val Gly Ile Gly Ala Met
            500                 505                 510

Phe Leu Gly Phe Leu Gly Ala Ala Gly Ser Thr Met Gly Ala Ala Ser
        515                 520                 525

Ile Thr Leu Thr Val Gln Ala Arg Gln Leu Leu Ser Gly Ile Val Gln
        530                 535                 540

Gln Gln Asn Asn Leu Leu Arg Ala Ile Glu Ala Gln Gln His Leu Leu
545                 550                 555                 560

Gln Leu Thr Val Trp Gly Ile Lys Gln Leu Gln Ala Arg Val Leu Ala
            565                 570                 575

Val Glu Arg Tyr Leu Lys Asp Gln Gln Leu Leu Gly Ile Trp Gly Cys
            580                 585                 590
```

-continued

Ser Gly Lys Leu Ile Cys Thr Thr Thr Val Pro Trp Asn Ala Ser Trp
            595                 600                 605

Ser Asn Lys Ser Leu Asp Ala Ile Trp Asn Asn Met Thr Trp Met Glu
    610                 615                 620

Trp Glu Arg Glu Ile Asp Asn Tyr Thr Gly Leu Ile Tyr Thr Leu Ile
625                 630                 635                 640

Glu Glu Ser Gln Asn Gln Gln Glu Lys Asn Glu Gln Glu Leu Leu Glu
            645                 650                 655

Leu Asp Lys Trp Ala Ser Leu Trp Asn Trp Phe Asp Ile Thr Lys Trp
            660                 665                 670

Leu Trp Tyr Ile Lys Ile Phe Ile Met Ile Val Gly Gly Leu Ile Gly
            675                 680                 685

Leu Arg Ile Val Phe Thr Val Leu Ser Ile Val Asn Arg Val Arg Gln
            690                 695                 700

Gly Tyr Ser Pro Leu Ser Phe Gln Thr His Leu Pro Ala Pro Arg Gly
705                 710                 715                 720

Pro Asp Arg Pro Glu Gly Ile Glu Glu Gly Gly Glu Arg Asp Arg
                725                 730                 735

Asp Arg Ser Gly Pro Leu Val Asp Gly Phe Leu Ala Ile Ile Trp Val
            740                 745                 750

Asp Leu Arg Ser Leu Cys Leu Phe Ser Tyr His Arg Leu Arg Asp Leu
            755                 760                 765

Leu Leu Ile Val Thr Arg Ile Val Glu Leu Leu Gly Arg Arg Gly Trp
            770                 775                 780

Glu Ala Leu Lys Tyr Trp Trp Asn Leu Leu Gln Tyr Trp Ser Gln Glu
785                 790                 795                 800

Leu Lys Asn Ser Ala Val Ser Leu Leu Asn Ala Thr Ala Ile Ala Val
            805                 810                 815

Ala Glu Gly Thr Asp Arg Ile Ile Glu Val Leu Gln Arg Ile Gly Arg
            820                 825                 830

Ala Ile Leu His Ile Pro Thr Arg Ile Arg Gln Gly Leu Glu Arg Ala
            835                 840                 845

Leu Leu
    850

<210> SEQ ID NO 5
<211> LENGTH: 851
<212> TYPE: PRT
<213> ORGANISM: Artificial Sequence
<220> FEATURE:
<223> OTHER INFORMATION: CRF01mos3.1 mosaic protein

<400> SEQUENCE: 5

Met Arg Val Arg Gly Ile Gln Met Asn Trp Pro Asn Leu Trp Lys Trp
1               5                   10                  15

Gly Thr Leu Ile Leu Gly Leu Val Ile Ile Cys Ser Ala Ser Asn Asn
            20                  25                  30

Leu Trp Val Thr Val Tyr Tyr Gly Val Pro Val Trp Arg Asp Ala Asp
        35                  40                  45

Thr Thr Leu Phe Cys Ala Ser Asp Ala Lys Ala His Met Thr Glu Val
    50                  55                  60

His Asn Val Trp Ala Thr His Ala Cys Val Pro Thr Asp Pro Asn Pro
65                  70                  75                  80

Gln Glu Ile Pro Leu Glu Asn Val Thr Glu Asn Phe Asn Met Trp Lys
                85                  90                  95

```
Asn Asn Met Val Glu Gln Met Gln Glu Asp Val Ile Ser Leu Trp Asp
        100                 105                 110
Gln Ser Leu Lys Pro Cys Val Lys Leu Thr Pro Leu Cys Val Thr Leu
        115                 120                 125
Asn Cys Thr Asn Ala Glu Trp His Asn Thr Thr Asn Gly Asn Ser Ser
        130                 135                 140
Ile Gly Asn Ile Thr Asp Glu Val Lys Asn Cys Thr Phe Asn Met Thr
145                 150                 155                 160
Thr Glu Ile Arg Gly Lys Gln Gln Lys Val His Ala Leu Phe Tyr Ala
                165                 170                 175
Leu Asp Ile Val Gln Met Lys Glu Asn Gly Ser Glu Tyr Arg Leu Ile
            180                 185                 190
Ser Cys Asn Thr Ser Val Ile Lys Gln Ala Cys Pro Lys Ile Ser Phe
        195                 200                 205
Asp Pro Ile Pro Ile His Tyr Cys Ala Pro Ala Gly Tyr Ala Ile Leu
        210                 215                 220
Lys Cys Asn Asp Lys Lys Phe Asn Gly Thr Gly Pro Cys Lys Asn Val
225                 230                 235                 240
Ser Thr Val Gln Cys Thr His Gly Ile Lys Pro Val Val Ser Thr Gln
                245                 250                 255
Leu Leu Leu Asn Gly Ser Leu Ala Glu Glu Ile Ile Ile Arg Ser
            260                 265                 270
Glu Asn Leu Thr Asn Asn Ala Lys Thr Ile Ile Val His Leu Asn Lys
        275                 280                 285
Ser Val Ser Ile Asn Cys Thr Arg Pro Ser Asn Asn Thr Arg Thr Ser
        290                 295                 300
Ile Arg Ile Gly Pro Gly Gln Met Phe Tyr Arg Thr Gly Asp Ile Ile
305                 310                 315                 320
Gly Asp Ile Arg Lys Ala Tyr Cys Glu Ile Asn Gly Thr Glu Trp Asn
                325                 330                 335
Glu Thr Leu Asn Gln Val Ala Lys Lys Leu Lys Glu His Phe Lys Asn
            340                 345                 350
Lys Thr Ile Val Phe Gln Pro Pro Ser Gly Gly Asp Leu Glu Thr Thr
        355                 360                 365
Met His His Phe Asn Cys Arg Gly Glu Phe Phe Tyr Cys Asn Thr Thr
        370                 375                 380
Lys Leu Phe Asn Ser Thr Glu Asn Gly Thr Met Glu Gly Arg Asn Thr
385                 390                 395                 400
Thr Ile Ile Leu Pro Cys Arg Ile Lys Gln Ile Ile Asn Met Trp Gln
                405                 410                 415
Gly Val Gly Gln Ala Met Tyr Ala Pro Pro Ile Ser Gly Ile Ile Asn
            420                 425                 430
Cys Thr Ser Asn Ile Thr Gly Ile Leu Leu Thr Arg Asp Gly Gly Asn
        435                 440                 445
Asn Asn Ala Thr Asn Glu Thr Phe Arg Pro Gly Gly Gly Asn Ile Lys
        450                 455                 460
Asp Asn Trp Arg Ser Glu Leu Tyr Lys Tyr Lys Val Val Gln Ile Glu
465                 470                 475                 480
Pro Leu Gly Ile Ala Pro Thr Arg Ala Lys Arg Arg Val Val Asp Arg
                485                 490                 495
Glu Lys Arg Ala Val Gly Ile Gly Ala Met Ile Phe Gly Phe Leu Gly
            500                 505                 510
```

Ala Ala Gly Ser Thr Met Gly Ala Ala Ser Ile Thr Leu Thr Val Gln
            515                 520                 525

Ala Arg Gln Leu Leu Ser Gly Ile Val Gln Gln Ser Asn Leu Leu
    530                 535                 540

Arg Ala Ile Glu Ala Gln Gln His Leu Leu Gln Leu Thr Val Trp Gly
545                 550                 555                 560

Ile Lys Gln Leu Gln Ala Arg Val Leu Ala Val Glu Arg Tyr Leu Lys
                565                 570                 575

Asp Gln Lys Phe Leu Gly Leu Trp Gly Cys Ser Gly Lys Ile Ile Cys
            580                 585                 590

Thr Thr Asn Val Pro Trp Asn Ser Thr Trp Ser Asn Lys Ser Tyr Glu
        595                 600                 605

Glu Ile Trp Asn Asn Met Thr Trp Ile Glu Trp Glu Lys Glu Ile Ser
    610                 615                 620

Asn Tyr Thr Asn Arg Ile Tyr Asp Leu Leu Thr Glu Ser Gln Asn Gln
625                 630                 635                 640

Gln Glu Arg Asn Glu Lys Asp Leu Leu Glu Leu Asp Lys Trp Ala Ser
                645                 650                 655

Leu Trp Asn Trp Phe Asp Ile Thr Lys Trp Leu Trp Tyr Ile Lys Ile
            660                 665                 670

Phe Ile Met Ile Val Gly Gly Leu Ile Gly Leu Arg Ile Ile Phe Ala
        675                 680                 685

Val Leu Ser Ile Val Asn Arg Val Arg Gln Gly Tyr Ser Pro Leu Ser
    690                 695                 700

Phe Gln Thr Pro Phe His Gln Gln Arg Glu Pro Asp Arg Pro Glu Gly
705                 710                 715                 720

Ile Glu Glu Glu Gly Gly Glu Gln Gly Arg Asp Arg Ser Val Arg Leu
                725                 730                 735

Val Ser Gly Phe Leu Ala Leu Ala Trp Asp Asp Leu Arg Ser Leu Cys
            740                 745                 750

Leu Phe Ser Tyr His Arg Leu Arg Asp Phe Ile Leu Ile Ala Thr Arg
        755                 760                 765

Thr Val Glu Leu Leu Gly His Ser Ser Leu Lys Gly Leu Arg Arg Gly
    770                 775                 780

Trp Glu Ser Leu Lys Tyr Leu Gly Asn Leu Leu Leu Tyr Trp Gly Gln
785                 790                 795                 800

Glu Leu Lys Thr Ser Ala Ile Ser Leu Leu Asp Ala Ile Ala Ile Thr
                805                 810                 815

Thr Ala Gly Trp Thr Asp Arg Val Ile Glu Val Ala Gln Arg Ala Trp
            820                 825                 830

Arg Ala Leu Leu His Ile Pro Arg Arg Ile Arg Gln Gly Leu Glu Arg
        835                 840                 845

Ala Leu Leu
    850

<210> SEQ ID NO 6
<211> LENGTH: 849
<212> TYPE: PRT
<213> ORGANISM: Artificial Sequence
<220> FEATURE:
<223> OTHER INFORMATION: Mmos3.1 mosaic protein

<400> SEQUENCE: 6

Met Arg Val Met Gly Ile Gln Arg Asn Tyr Gln His Leu Trp Arg Trp
1               5                   10                  15

```
Gly Thr Met Leu Leu Gly Met Leu Met Ile Cys Ser Ala Ala Glu Gln
             20                  25                  30

Leu Trp Val Thr Val Tyr Tyr Gly Val Pro Val Trp Lys Glu Ala Thr
         35                  40                  45

Thr Thr Leu Phe Cys Ala Ser Asp Ala Lys Ser Tyr Lys Thr Glu Ala
     50                  55                  60

His Asn Ile Trp Ala Thr His Ala Cys Val Pro Thr Asp Pro Asn Pro
 65                  70                  75                  80

Gln Glu Val Val Leu Glu Asn Val Thr Glu Asn Phe Asn Met Trp Lys
                 85                  90                  95

Asn Asn Met Val Glu Gln Met His Glu Asp Ile Ile Ser Leu Trp Asp
             100                 105                 110

Glu Ser Leu Lys Pro Cys Val Lys Leu Thr Pro Leu Cys Val Thr Leu
         115                 120                 125

Asn Cys Thr Asn Tyr Glu Gly Asn Gly Asn Tyr Thr Thr Val Gln Asn
     130                 135                 140

Asn Thr Ile Gly Glu Ile Lys Asn Cys Ser Phe Asn Ile Thr Thr Ala
145                 150                 155                 160

Ile Arg Asp Lys Val Gln Lys Thr Tyr Ala Leu Phe Tyr Arg Leu Asp
                 165                 170                 175

Val Val Pro Ile Lys Asp Thr Asn Asp Ser Arg Thr Tyr Arg Leu Ile
             180                 185                 190

Asn Cys Asn Thr Ser Val Ile Thr Gln Ala Cys Pro Lys Val Ser Phe
         195                 200                 205

Glu Pro Ile Pro Ile His Tyr Cys Ala Pro Ala Gly Phe Ala Ile Leu
     210                 215                 220

Lys Cys Asn Asn Lys Lys Phe Asn Gly Thr Gly Pro Cys Lys Asn Val
225                 230                 235                 240

Ser Thr Val Gln Cys Thr His Gly Ile Arg Pro Val Val Ser Thr Gln
                 245                 250                 255

Leu Leu Leu Asn Gly Ser Leu Ala Glu Glu Val Val Ile Arg Ser
             260                 265                 270

Glu Asn Ile Thr Asp Asn Ala Lys Thr Ile Ile Val Gln Leu Asn Glu
         275                 280                 285

Ser Val Ile Ile Asn Cys Thr Arg Pro Asn Asn Asn Thr Arg Lys Ser
     290                 295                 300

Ile His Ile Gly Pro Gly Arg Ala Phe Tyr Ala Thr Gly Asp Ile Ile
305                 310                 315                 320

Gly Asp Ile Arg Arg Ala His Cys Asn Leu Ser Arg Thr Ser Trp Asn
                 325                 330                 335

Asn Thr Leu Lys Gln Ile Val Glu Lys Leu Arg Glu Gln Phe Gly Asn
             340                 345                 350

Lys Thr Ile Val Phe Asn Gln Ser Ser Gly Gly Asp Pro Glu Ile Val
         355                 360                 365

Met His Ser Phe Asn Cys Gly Gly Glu Phe Phe Tyr Cys Asn Ser Thr
     370                 375                 380

Gln Leu Phe Asn Ser Thr Trp His Ala Asn Gly Thr Trp Lys Asn Thr
385                 390                 395                 400

Glu Gly Ala Asp Asn Asn Ile Thr Leu Pro Cys Arg Ile Lys Gln Ile
                 405                 410                 415

Ile Asn Met Trp Gln Glu Val Gly Lys Ala Met Tyr Ala Pro Pro Ile
             420                 425                 430

Arg Gly Gln Ile Arg Cys Ser Ser Asn Ile Thr Gly Leu Leu Leu Thr
```

```
                435                 440                 445
Arg Asp Gly Gly Asn His Thr Ser Glu Thr Glu Ile Phe Arg Pro Gly
    450                 455                 460

Gly Gly Asp Met Arg Asp Asn Trp Arg Ser Glu Leu Tyr Lys Tyr Lys
465                 470                 475                 480

Val Val Lys Ile Glu Pro Leu Gly Val Ala Pro Thr Lys Ala Lys Arg
                485                 490                 495

Arg Val Val Gln Arg Glu Lys Arg Ala Val Gly Leu Gly Ala Met Phe
            500                 505                 510

Leu Gly Phe Leu Gly Ala Ala Gly Ser Thr Met Gly Ala Ala Ser Leu
        515                 520                 525

Thr Leu Thr Val Gln Ala Arg Leu Leu Leu Ser Gly Ile Val Gln Gln
    530                 535                 540

Gln Asn Asn Leu Leu Arg Ala Ile Glu Ala Gln Gln His Leu Leu Gln
545                 550                 555                 560

Leu Thr Val Trp Gly Ile Lys Gln Leu Gln Ala Arg Ile Leu Ala Val
                565                 570                 575

Glu Arg Tyr Leu Lys Asp Gln Gln Leu Leu Gly Ile Trp Gly Cys Ser
            580                 585                 590

Gly Lys Leu Ile Cys Thr Thr Thr Val Pro Trp Asn Ser Ser Trp Ser
        595                 600                 605

Asn Arg Ser Leu Asn Asp Ile Trp Gln Asn Met Thr Trp Met Glu Trp
610                 615                 620

Glu Arg Glu Ile Asp Asn Tyr Thr Gly Leu Ile Tyr Thr Leu Ile Glu
625                 630                 635                 640

Glu Ser Gln Asn Gln Gln Glu Lys Asn Glu Gln Glu Leu Leu Glu Leu
                645                 650                 655

Asp Lys Trp Ala Ser Leu Trp Asn Trp Phe Asp Ile Thr Lys Trp Leu
            660                 665                 670

Trp Tyr Ile Lys Ile Phe Ile Met Ile Val Gly Gly Leu Ile Gly Leu
        675                 680                 685

Arg Ile Val Phe Ala Val Leu Ser Leu Val Asn Arg Val Arg Gln Gly
    690                 695                 700

Tyr Ser Pro Leu Ser Phe Gln Thr Leu Leu Pro Ala Pro Arg Gly Pro
705                 710                 715                 720

Asp Arg Pro Glu Gly Ile Glu Glu Gly Gly Glu Arg Gly Arg Asp
                725                 730                 735

Arg Ser Ile Arg Leu Val Asn Gly Phe Ser Ala Leu Ile Trp Asp Asp
            740                 745                 750

Leu Arg Asn Leu Cys Leu Phe Ser Tyr His Arg Leu Arg Asp Leu Ile
        755                 760                 765

Leu Ile Ala Ala Arg Ile Val Glu Leu Leu Gly Arg Arg Gly Trp Glu
    770                 775                 780

Ala Leu Lys Tyr Trp Trp Asn Leu Leu Gln Tyr Trp Ser Gln Glu Leu
785                 790                 795                 800

Lys Asn Ser Ala Val Ser Leu Leu Asn Ala Thr Ala Ile Ala Val Ala
                805                 810                 815

Glu Gly Thr Asp Arg Ile Ile Glu Val Val Gln Arg Ile Cys Arg Ala
            820                 825                 830

Ile Leu Asn Ile Pro Arg Arg Ile Arg Gln Gly Phe Glu Ala Ala Leu
        835                 840                 845

Gln
```

-continued

```
<210> SEQ ID NO 7
<211> LENGTH: 853
<212> TYPE: PRT
<213> ORGANISM: Artificial Sequence
<220> FEATURE:
<223> OTHER INFORMATION: Mmos3.2 mosaic protein

<400> SEQUENCE: 7

Met Arg Val Arg Gly Ile Leu Arg Asn Tyr Gln Gln Trp Trp Ile Trp
1               5                   10                  15

Gly Ile Leu Gly Phe Trp Met Leu Met Ile Cys Asn Val Val Gly Asn
                20                  25                  30

Leu Trp Val Thr Ile Tyr Tyr Gly Val Pro Val Trp Lys Glu Ala Lys
            35                  40                  45

Thr Thr Leu Phe Cys Ala Ser Asp Ala Lys Ala Tyr Glu Lys Glu Val
        50                  55                  60

His Asn Val Trp Ala Thr His Ala Cys Val Pro Thr Asp Pro Asn Pro
65                  70                  75                  80

Gln Glu Met Val Leu Glu Asn Val Thr Glu Asn Phe Asn Met Trp Lys
                85                  90                  95

Asn Asp Met Val Asp Gln Met His Glu Asp Ile Ile Ser Leu Trp Asp
                100                 105                 110

Gln Ser Leu Lys Pro Cys Val Lys Leu Thr Pro Leu Cys Val Thr Leu
            115                 120                 125

Asn Cys Ser Asn Val Asn Ser Asn Arg Thr Val Asp Asn Ala Thr Gln
        130                 135                 140

Gly Glu Met Lys Asn Cys Ser Phe Asn Ile Thr Thr Glu Leu Arg Asp
145                 150                 155                 160

Lys Lys Gln Lys Val Tyr Ala Leu Phe Tyr Lys Leu Asp Ile Leu Pro
                165                 170                 175

Leu Asn Gly Asn Asn Asp Ser Asn Glu Tyr Arg Leu Ile Asn Cys Asn
                180                 185                 190

Thr Ser Ala Ile Thr Gln Ala Cys Pro Lys Val Ser Phe Asp Pro Ile
            195                 200                 205

Pro Ile His Tyr Cys Ala Pro Ala Gly Tyr Ala Ile Leu Lys Cys Asn
        210                 215                 220

Asn Lys Thr Phe Asn Gly Thr Gly Pro Cys Asn Asn Val Ser Thr Val
225                 230                 235                 240

Gln Cys Thr His Gly Ile Lys Pro Val Val Ser Thr Gln Leu Leu Leu
                245                 250                 255

Asn Gly Ser Leu Ala Glu Glu Asp Ile Ile Arg Ser Glu Asn Leu
                260                 265                 270

Thr Asn Asn Val Lys Thr Ile Ile Val His Leu Asn Glu Ser Val Glu
            275                 280                 285

Ile Val Cys Thr Arg Pro Asn Asn Asn Thr Arg Lys Ser Ile Arg Ile
        290                 295                 300

Gly Pro Gly Gln Thr Phe Tyr Ala Thr Gly Glu Ile Ile Gly Asp Ile
305                 310                 315                 320

Arg Gln Ala His Cys Asn Ile Ser Glu Tyr Lys Trp Asn Lys Thr Leu
                325                 330                 335

Gln Arg Val Ser Glu Lys Leu Ala Glu Tyr Phe Pro Asn Asp Thr Ile
            340                 345                 350

Lys Phe Ala Pro Ser Ser Gly Gly Asp Leu Glu Ile Thr Thr His Ser
        355                 360                 365
```

```
Phe Asn Cys Arg Gly Glu Phe Phe Tyr Cys Asn Thr Ser Gly Leu Phe
370                 375                 380

Asn Gly Thr Tyr Asn Ser Thr Tyr Lys Thr Asn Thr Thr Glu Ser Asn
385                 390                 395                 400

Ala Thr Ile Thr Ile Pro Cys Arg Ile Lys Gln Ile Ile Asn Met Trp
        405                 410                 415

Gln Glu Val Gly Arg Ala Met Tyr Ala Pro Pro Ile Ala Gly Asn Ile
        420                 425                 430

Thr Cys Lys Ser Asn Ile Thr Gly Leu Leu Thr Arg Asp Gly Gly
        435                 440                 445

Asn Ser Glu Asn Asn Thr Lys Glu Thr Phe Arg Pro Gly Gly Gly Asp
450                 455                 460

Met Arg Asp Asn Trp Arg Ser Glu Leu Tyr Lys Tyr Lys Val Val Glu
465                 470                 475                 480

Ile Lys Pro Leu Gly Ile Ala Pro Thr Arg Ala Lys Arg Arg Val Val
                485                 490                 495

Glu Arg Glu Lys Arg Ala Val Gly Ile Gly Ala Val Phe Leu Gly Phe
                500                 505                 510

Leu Gly Ala Ala Gly Ser Thr Met Gly Ala Ala Ser Ile Thr Leu Thr
        515                 520                 525

Val Gln Ala Arg Gln Leu Leu Ser Gly Ile Val Gln Gln Gln Ser Asn
530                 535                 540

Leu Leu Arg Ala Ile Glu Ala Gln Gln His Met Leu Gln Leu Thr Val
545                 550                 555                 560

Trp Gly Ile Lys Gln Leu Gln Thr Arg Val Leu Ala Ile Glu Arg Tyr
                565                 570                 575

Leu Arg Asp Gln Gln Leu Leu Gly Ile Trp Gly Cys Ser Gly Lys Leu
                580                 585                 590

Ile Cys Thr Thr Asn Val Pro Trp Asn Ser Ser Trp Ser Asn Lys Ser
        595                 600                 605

Tyr Asp Glu Ile Trp Asp Asn Met Thr Trp Met Gln Trp Asp Arg Glu
                610                 615                 620

Ile Ser Asn Tyr Ser Asp Thr Ile Tyr Arg Leu Leu Glu Glu Ser Gln
625                 630                 635                 640

Asn Gln Gln Glu Lys Asn Glu Gln Asp Leu Leu Ala Leu Asp Lys Trp
                645                 650                 655

Ala Asn Leu Trp Asn Trp Phe Asp Ile Ser Asn Trp Leu Trp Tyr Ile
                660                 665                 670

Lys Ile Phe Ile Met Ile Val Gly Gly Leu Ile Gly Leu Arg Ile Val
                675                 680                 685

Phe Ala Val Leu Ser Ile Ile Asn Arg Val Arg Gln Gly Tyr Ser Pro
690                 695                 700

Leu Ser Phe Gln Thr Leu Thr Pro Asn Pro Arg Gly Leu Asp Arg Pro
705                 710                 715                 720

Gly Arg Ile Glu Glu Glu Gly Gly Glu Gln Asp Arg Asp Arg Ser Ile
                725                 730                 735

Arg Leu Val Ser Gly Phe Leu Ala Leu Ala Trp Asp Asp Leu Arg Ser
        740                 745                 750

Leu Cys Leu Phe Ser Tyr His Arg Leu Arg Asp Phe Ile Leu Ile Ala
        755                 760                 765

Ala Arg Thr Val Glu Leu Leu Gly Arg Ser Ser Leu Lys Gly Leu Arg
770                 775                 780

Leu Gly Trp Glu Gly Leu Lys Tyr Leu Trp Asn Leu Leu Gln Tyr Trp
```

-continued

```
                785                 790                 795                 800
Ile Gln Glu Leu Lys Asn Ser Ala Ile Ser Leu Leu Asp Thr Ile Ala
                    805                 810                 815

Ile Ala Val Ala Glu Gly Thr Asp Arg Val Ile Glu Val Val Gln Arg
                820                 825                 830

Ile Cys Arg Ala Ile Arg Asn Ile Pro Arg Arg Ile Arg Gln Gly Phe
                835                 840                 845

Glu Arg Ala Leu Leu
    850

<210> SEQ ID NO 8
<211> LENGTH: 862
<212> TYPE: PRT
<213> ORGANISM: Artificial Sequence
<220> FEATURE:
<223> OTHER INFORMATION: Mmos3.3 mosaic protein

<400> SEQUENCE: 8

Met Arg Val Lys Glu Thr Gln Met Asn Trp Pro Asn Leu Trp Lys Trp
1               5                   10                  15

Gly Thr Leu Ile Leu Gly Leu Val Ile Ile Cys Ser Ala Ser Asp Asn
                20                  25                  30

Leu Trp Val Thr Val Tyr Tyr Gly Val Pro Val Trp Arg Asp Ala Asp
            35                  40                  45

Thr Thr Leu Phe Cys Ala Ser Asp Ala Lys Ala Tyr Asp Thr Glu Val
        50                  55                  60

His Asn Val Trp Ala Thr His Ala Cys Val Pro Thr Asp Pro Asn Pro
65                  70                  75                  80

Gln Glu Ile His Leu Glu Asn Val Thr Glu Asn Phe Asn Met Trp Lys
                85                  90                  95

Asn Asn Met Val Glu Gln Met Gln Glu Asp Val Ile Ser Leu Trp Asp
                100                 105                 110

Gln Ser Leu Lys Pro Cys Val Lys Leu Thr Pro Leu Cys Val Thr Leu
            115                 120                 125

Asn Cys Thr Lys Ala Asn Leu Thr Asn Ile Asn Glu Thr Thr Ala Ser
        130                 135                 140

Asn Gly Ile Gly Asn Ile Thr Asp Glu Val Arg Asn Cys Ser Phe Asn
145                 150                 155                 160

Met Thr Thr Leu Leu Ser Asp Lys Lys Arg Leu Val His Ala Leu Phe
                165                 170                 175

Tyr Lys Leu Asp Ile Val Pro Ile Lys Asp Asn Gln Asn Ser Ser Val
                180                 185                 190

Ser Ser Gly Glu Tyr Arg Leu Ile Asn Cys Asn Thr Ser Val Ile Lys
            195                 200                 205

Gln Ala Cys Pro Lys Val Thr Phe Asp Pro Ile Pro Ile His Tyr Cys
        210                 215                 220

Thr Pro Ala Gly Tyr Ala Ile Leu Lys Cys Asn Asp Lys Asn Phe Asn
225                 230                 235                 240

Gly Thr Gly Pro Cys Lys Asn Val Ser Ser Val Gln Cys Thr His Gly
                245                 250                 255

Ile Lys Pro Val Val Ser Thr Gln Leu Leu Leu Asn Gly Ser Leu Ala
                260                 265                 270

Glu Glu Glu Ile Ile Ile Arg Ser Glu Asn Leu Thr Asn Asn Ala Lys
            275                 280                 285

Thr Ile Ile Val His Leu Asn Lys Ser Val Glu Ile Asn Cys Thr Arg
```

```
                290                 295                 300
Pro Ser Asn Asn Thr Arg Thr Ser Val Arg Ile Gly Pro Gly Gln Val
305                 310                 315                 320

Phe Tyr Arg Thr Gly Asp Ile Ile Gly Asp Ile Arg Gln Ala Tyr Cys
                325                 330                 335

Glu Ile Asn Gly Thr Lys Trp Asn Glu Thr Leu Arg Gln Val Ala Lys
                340                 345                 350

Lys Leu Lys Glu His Phe Asn Lys Thr Ile Ile Phe Gln Pro Pro Ser
                355                 360                 365

Gly Gly Asp Leu Glu Ile Thr Met His His Phe Asn Cys Arg Gly Glu
                370                 375                 380

Phe Phe Tyr Cys Asn Thr Thr Lys Leu Phe Asn Ser Thr Trp Ile Gly
385                 390                 395                 400

Asn Glu Thr Met Val Glu Gly Asn Asn Asn Asp Thr Ile Ile Leu Pro
                405                 410                 415

Cys Arg Ile Lys Gln Ile Ile Asn Met Trp Gln Gly Val Gly Gln Ala
                420                 425                 430

Met Tyr Ala Pro Pro Ile Ser Gly Ile Ile Asn Cys Val Ser Asn Ile
                435                 440                 445

Thr Gly Ile Leu Leu Thr Arg Asp Gly Gly Ser Gly Asp Asn Ala Thr
                450                 455                 460

Glu Thr Phe Arg Pro Gly Gly Gly Asn Ile Lys Asp Asn Trp Arg Ser
465                 470                 475                 480

Glu Leu Tyr Lys Tyr Lys Val Val Glu Ile Glu Pro Leu Gly Ile Ala
                485                 490                 495

Pro Thr Lys Ala Lys Arg Arg Val Val Glu Arg Glu Lys Arg Ala Val
                500                 505                 510

Gly Ile Gly Ala Met Ile Phe Gly Phe Leu Gly Ala Ala Gly Ser Thr
                515                 520                 525

Met Gly Ala Ala Ser Ile Thr Leu Thr Val Gln Ala Arg Gln Leu Leu
                530                 535                 540

Ser Gly Ile Val Gln Gln Gln Ser Asn Leu Leu Arg Ala Ile Glu Ala
545                 550                 555                 560

Gln Gln His Leu Leu Gln Leu Thr Val Trp Gly Ile Lys Gln Leu Gln
                565                 570                 575

Ala Arg Val Leu Ala Val Glu Arg Tyr Leu Lys Asp Gln Lys Phe Leu
                580                 585                 590

Gly Leu Trp Gly Cys Ser Gly Lys Ile Ile Cys Thr Thr Ala Val Pro
                595                 600                 605

Trp Asn Ser Thr Trp Ser Asn Lys Ser Tyr Glu Glu Ile Trp Asn Asn
                610                 615                 620

Met Thr Trp Ile Glu Trp Glu Arg Glu Ile Ser Asn Tyr Thr Ser Gln
625                 630                 635                 640

Ile Tyr Glu Ile Leu Thr Glu Ser Gln Asn Gln Gln Asp Arg Asn Glu
                645                 650                 655

Lys Asp Leu Leu Glu Leu Asp Lys Trp Ala Ser Leu Trp Asn Trp Phe
                660                 665                 670

Asp Ile Thr Arg Trp Leu Trp Tyr Ile Lys Ile Phe Ile Met Ile Val
                675                 680                 685

Gly Gly Leu Ile Gly Leu Arg Ile Ile Phe Ala Val Leu Ser Ile Val
                690                 695                 700

Asn Arg Val Arg Gln Gly Tyr Ser Pro Leu Ser Phe Gln Thr Pro Thr
705                 710                 715                 720
```

```
His His Gln Arg Glu Pro Asp Arg Pro Glu Arg Ile Glu Glu Glu Gly
                725             730             735

Gly Glu Gln Gly Arg Asp Arg Ser Val Arg Leu Val Ser Gly Phe Leu
            740             745             750

Ala Leu Ala Trp Asp Asp Leu Arg Ser Leu Cys Leu Phe Ser Tyr His
            755             760             765

Arg Leu Arg Asp Leu Leu Leu Ile Val Ala Arg Thr Val Glu Leu Leu
    770             775             780

Gly His Ser Ser Leu Lys Gly Leu Arg Arg Gly Trp Glu Gly Leu Lys
785             790             795             800

Tyr Leu Gly Asn Leu Leu Leu Tyr Trp Gly Gln Glu Leu Lys Ile Ser
            805             810             815

Ala Ile Ser Leu Leu Asp Ala Thr Ala Ile Ala Val Ala Gly Trp Thr
            820             825             830

Asp Arg Val Ile Glu Val Ala Gln Arg Ala Trp Arg Ala Ile Leu His
            835             840             845

Ile Pro Arg Arg Ile Arg Gln Gly Leu Glu Arg Ala Leu Leu
    850             855             860

<210> SEQ ID NO 9
<211> LENGTH: 23
<212> TYPE: PRT
<213> ORGANISM: Artificial Sequence
<220> FEATURE:
<223> OTHER INFORMATION: tPA leader peptide

<400> SEQUENCE: 9

Met Asp Ala Met Lys Arg Gly Leu Cys Cys Val Leu Leu Leu Cys Gly
1               5                   10                  15

Ala Val Phe Val Ser Ala Arg
            20
```